(12) United States Patent
Ruiz

(10) Patent No.: US 11,813,204 B2
(45) Date of Patent: *Nov. 14, 2023

(54) TILT MECHANISMS FOR MEDICAL SYSTEMS AND APPLICATIONS

(71) Applicant: Auris Health, Inc., Redwood City, CA (US)

(72) Inventor: Christian de Jesus Ruiz, Redwood City, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/929,684

(22) Filed: Sep. 3, 2022

(65) Prior Publication Data

US 2022/0409462 A1 Dec. 29, 2022

Related U.S. Application Data

(63) Continuation of application No. 17/202,220, filed on Mar. 15, 2021, now Pat. No. 11,432,981, which is a
(Continued)

(51) Int. Cl.
*A61G 13/04* (2006.01)
*B25J 11/00* (2006.01)
(Continued)

(52) U.S. Cl.
CPC ............. *A61G 13/04* (2013.01); *A61B 34/30* (2016.02); *B25J 9/0096* (2013.01); *B25J 11/009* (2013.01);
(Continued)

(58) Field of Classification Search
CPC ....... A61G 13/04; B25J 11/009; B25J 9/0096; A61B 34/30; A61B 2034/302; A61B 2034/303; A61B 2034/301
(Continued)

(56) References Cited

U.S. PATENT DOCUMENTS 3,997,926 A 12/1976 England
4,831,547 A * 5/1989 Ishiguro .................... B25J 9/06
901/6
(Continued)

FOREIGN PATENT DOCUMENTS

CN 1973804 A 6/2007
CN 102727358 A 10/2012
(Continued)

OTHER PUBLICATIONS

International search report and written opinion dated Jul. 24, 2020 for PCT/US20/21200.
(Continued)

*Primary Examiner* — Muhammad Ijaz
(74) *Attorney, Agent, or Firm* — Conley Rose, P.C.; Gayatry S. Nair

(57) ABSTRACT

A robotic medical system can include a patient platform. The patient platform includes a tilt mechanism. The tilt mechanism can include a lateral tilt mechanism and a longitudinal tilt mechanism. The lateral tilt mechanism can include a tilt plate and a pivot housing. A linear actuator mounted on the tilt plate can apply a linear force to the pivot housing. The lateral tilt mechanism can also include a first linear guide that extends along a first axis, and the pivot housing can translate along the first linear guide. Application of the linear force to the pivot housing tilts the tilt plate by causing the pivot housing to translate along the first linear guide.

20 Claims, 35 Drawing Sheets

Related U.S. Application Data continuation of application No. 16/810,469, filed on Mar. 5, 2020, now Pat. No. 10,945,904.

(60) Provisional application No. 62/815,848, filed on Mar. 8, 2019.

(51) Int. Cl.
*B25J 9/00* (2006.01)
*A61B 34/30* (2016.01)

(52) U.S. Cl.
CPC ... *A61B 2034/301* (2016.02); *A61B 2034/302* (2016.02); *A61B 2034/303* (2016.02)

(58) Field of Classification Search
USPC .................................................. 248/370, 371
See application file for complete search history.

(56) References Cited

U.S. PATENT DOCUMENTS

| | | | |
|---|---|---|---|
| 4,878,494 A | 11/1989 | Phillips et al. | |
| 5,013,018 A | 5/1991 | Sicek | |
| 5,160,106 A | 11/1992 | Moniok | |
| 5,184,601 A * | 2/1993 | Putman | A61B 34/30 901/17 |
| 5,272,776 A * | 12/1993 | Kitamura | A61B 5/055 5/601 |
| 5,404,604 A | 4/1995 | Has et al. | |
| 5,405,604 A | 4/1995 | Hall | |
| 5,528,782 A | 6/1996 | Pfeuffer et al. | |
| 5,555,897 A | 9/1996 | Lathrop, Jr. et al. | |
| 5,571,072 A | 11/1996 | Kronner | |
| 5,762,458 A | 6/1998 | Wang et al. | |
| 5,791,233 A | 8/1998 | Knapp et al. | |
| 5,814,038 A | 9/1998 | Jensen et al. | |
| 5,926,875 A | 7/1999 | Okamoto et al. | |
| 5,944,476 A | 8/1999 | Bacchi et al. | |
| 6,170,102 B1 | 1/2001 | Kreuzer | |
| 6,202,230 B1 | 3/2001 | Borders | |
| 6,620,174 B2 | 9/2003 | Jensen et al. | |
| 6,640,363 B1 * | 11/2003 | Pattee | A61B 6/0487 5/607 |
| 6,676,669 B2 | 1/2004 | Charles et al. | |
| 6,681,423 B2 | 1/2004 | Zachrisson | |
| 6,788,018 B1 | 9/2004 | Blumenkranz | |
| 6,804,581 B2 | 10/2004 | Wang | |
| 7,025,761 B2 | 4/2006 | Wang et al. | |
| 7,074,179 B2 | 7/2006 | Wang et al. | |
| 7,763,015 B2 | 7/2010 | Cooper et al. | |
| 7,979,157 B2 | 7/2011 | Anvari | |
| 7,996,110 B2 | 8/2011 | Lipow et al. | |
| 8,142,420 B2 | 3/2012 | Schena | |
| 8,230,863 B2 | 7/2012 | Ravikumar et al. | |
| 8,343,096 B2 | 1/2013 | Kirschenman et al. | |
| 8,348,931 B2 | 1/2013 | Cooper et al. | |
| 8,400,094 B2 | 3/2013 | Schena | |
| 8,414,598 B2 | 4/2013 | Brock et al. | |
| 8,425,404 B2 | 4/2013 | Wilson et al. | |
| 8,469,945 B2 | 6/2013 | Schena | |
| 8,506,556 B2 | 8/2013 | Schena | |
| 8,512,353 B2 | 8/2013 | Rosielle et al. | |
| 8,515,576 B2 | 8/2013 | Lipow et al. | |
| 8,641,698 B2 | 2/2014 | Sanchez et al. | |
| 8,911,429 B2 | 12/2014 | Olds et al. | |
| 8,960,622 B2 | 2/2015 | von Pechmann et al. | |
| 8,968,333 B2 | 3/2015 | Yu et al. | |
| 9,023,060 B2 | 5/2015 | Cooper et al. | |
| 9,259,281 B2 | 2/2016 | Griffiths et al. | |
| 9,504,604 B2 | 11/2016 | Alvarez | |
| 9,554,865 B2 | 1/2017 | Olds et al. | |
| 9,561,083 B2 | 2/2017 | Yu et al. | |
| 9,615,889 B2 | 4/2017 | Jensen | |
| 9,622,827 B2 * | 4/2017 | Yu | A61G 7/008 |
| 9,636,184 B2 | 5/2017 | Lee et al. | |
| 9,713,499 B2 | 7/2017 | Bar et al. | |
| 9,713,509 B2 | 7/2017 | Schuh et al. | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,788,910 B2 | 10/2017 | Schuh | |
| 9,795,454 B2 | 10/2017 | Seeber et al. | |
| 9,820,819 B2 | 11/2017 | Olson | |
| 9,844,412 B2 | 12/2017 | Bogusky et al. | |
| 9,850,924 B2 | 12/2017 | Vogtherr et al. | |
| 9,867,635 B2 | 1/2018 | Alvarez et al. | |
| 9,907,458 B2 | 3/2018 | Schena | |
| 9,918,681 B2 | 3/2018 | Wallace et al. | |
| 9,931,025 B1 | 4/2018 | Graetzel et al. | |
| 9,949,749 B2 | 4/2018 | Noonan et al. | |
| 9,955,938 B2 | 5/2018 | Shah | |
| 9,962,228 B2 | 5/2018 | Schuh et al. | |
| 9,980,785 B2 | 5/2018 | Schuh | |
| 9,993,313 B2 | 6/2018 | Schuh et al. | |
| 9,999,478 B1 | 6/2018 | Griffiths | |
| 10,016,900 B1 | 7/2018 | Meyer et al. | |
| 10,022,192 B1 | 7/2018 | Ummalaneni | |
| 10,080,576 B2 | 9/2018 | Romo et al. | |
| 10,136,959 B2 | 11/2018 | Mintz et al. | |
| 10,145,747 B1 | 12/2018 | Lin et al. | |
| 10,149,720 B2 | 12/2018 | Romo | |
| 10,159,532 B1 | 12/2018 | Ummalaneni et al. | |
| 10,159,533 B2 | 12/2018 | Moll et al. | |
| 10,169,875 B2 | 1/2019 | Mintz et al. | |
| 10,219,874 B2 | 3/2019 | Yu et al. | |
| 10,231,793 B2 | 3/2019 | Romo | |
| 10,231,867 B2 | 3/2019 | Alvarez et al. | |
| 10,244,926 B2 | 4/2019 | Noonan et al. | |
| 10,285,574 B2 | 5/2019 | Landey et al. | |
| 10,299,870 B2 | 5/2019 | Connolly et al. | |
| 10,314,463 B2 | 6/2019 | Agrawal et al. | |
| 10,383,765 B2 | 8/2019 | Alvarez et al. | |
| 10,398,518 B2 | 9/2019 | Yu et al. | |
| 10,405,939 B2 | 9/2019 | Romo et al. | |
| 10,405,940 B2 | 9/2019 | Romo | |
| 10,426,559 B2 | 10/2019 | Graetzel et al. | |
| 10,426,661 B2 | 10/2019 | Kintz | |
| 10,434,660 B2 | 10/2019 | Meyer | |
| 10,464,209 B2 | 11/2019 | Ho et al. | |
| 10,470,830 B2 | 11/2019 | Hill | |
| 10,482,599 B2 | 11/2019 | Mintz et al. | |
| 10,493,241 B2 | 12/2019 | Jiang | |
| 10,500,001 B2 | 12/2019 | Yu et al. | |
| 10,517,692 B2 | 12/2019 | Eyre et al. | |
| 10,524,866 B2 | 1/2020 | Srinivasan | |
| 10,539,478 B2 | 1/2020 | Lin | |
| 10,543,048 B2 | 1/2020 | Noonan et al. | |
| 10,555,778 B2 | 2/2020 | Ummalaneni et al. | |
| 10,631,949 B2 | 4/2020 | Schuh et al. | |
| 10,639,108 B2 | 5/2020 | Romo et al. | |
| 10,639,109 B2 | 5/2020 | Bovay et al. | |
| 10,639,114 B2 | 5/2020 | Schuh | |
| 10,667,871 B2 | 6/2020 | Romo et al. | |
| 10,667,875 B2 | 6/2020 | DeFonzo | |
| 10,682,189 B2 | 6/2020 | Schuh et al. | |
| 10,702,348 B2 | 7/2020 | Moll et al. | |
| 10,718,481 B2 | 7/2020 | Jenkins | |
| 10,743,751 B2 | 8/2020 | Landey | |
| 10,744,035 B2 | 8/2020 | Alvarez et al. | |
| 2002/0162928 A1 | 11/2002 | Nguyen | |
| 2002/0165524 A1 | 11/2002 | Sanchez et al. | |
| 2002/0170116 A1 | 11/2002 | Borders | |
| 2003/0191455 A1 | 10/2003 | Sanchez et al. | |
| 2004/0172758 A1 | 9/2004 | Alakkat | |
| 2004/0243147 A1 | 12/2004 | Lipow | |
| 2004/0261179 A1 | 12/2004 | Blumenkranz | |
| 2005/0015878 A1 | 1/2005 | Bannister et al. | |
| 2005/0222554 A1 | 10/2005 | Wallace et al. | |
| 2006/0069383 A1 | 3/2006 | Bogaerts | |
| 2006/0149418 A1 | 7/2006 | Anvari | |
| 2008/0039867 A1 | 2/2008 | Feussner | |
| 2008/0167750 A1 | 7/2008 | Stahler | |

(56) References Cited

U.S. PATENT DOCUMENTS

| | | |
|---|---|---|
| 2010/0185211 A1 | 7/2010 | Herman |
| 2010/0204713 A1 | 8/2010 | Ruiz |
| 2010/0286712 A1 | 11/2010 | Won et al. |
| 2011/0257786 A1 | 10/2011 | Caron |
| 2012/0066832 A1* | 3/2012 | Poulos .................. A61G 7/005 5/83.1 |
| 2012/0266379 A1 | 10/2012 | Hushek |
| 2013/0053866 A1 | 2/2013 | Leung et al. |
| 2013/0096576 A1 | 4/2013 | Cooper |
| 2013/0131695 A1 | 5/2013 | Scarfogliero et al. |
| 2013/0221039 A1 | 8/2013 | Shah |
| 2013/0255425 A1 | 10/2013 | Schena |
| 2013/0338679 A1 | 12/2013 | Rosielle et al. |
| 2014/0142591 A1 | 5/2014 | Alvarez et al. |
| 2014/0180309 A1 | 6/2014 | Seeber et al. |
| 2014/0188132 A1 | 7/2014 | Kang |
| 2014/0249546 A1 | 9/2014 | Shvartsberg et al. |
| 2014/0357984 A1 | 12/2014 | Wallace et al. |
| 2015/0038981 A1 | 2/2015 | Kilroy et al. |
| 2015/0239082 A1 | 8/2015 | Krouglicof |
| 2015/0335389 A1 | 11/2015 | Greenberg |
| 2016/0001038 A1 | 1/2016 | Romo et al. |
| 2016/0157942 A1 | 6/2016 | Gombert |
| 2016/0270865 A1 | 9/2016 | Landey et al. |
| 2016/0287279 A1 | 10/2016 | Bovay et al. |
| 2016/0346052 A1 | 12/2016 | Rosielle et al. |
| 2016/0374771 A1* | 12/2016 | Mirbagheri ............ A61G 13/06 606/130 |
| 2017/0007337 A1 | 1/2017 | Dan |
| 2017/0045807 A1 | 2/2017 | Ye |
| 2017/0071692 A1 | 3/2017 | Taylor et al. |
| 2017/0071693 A1 | 3/2017 | Taylor et al. |
| 2017/0135771 A1 | 5/2017 | Auld et al. |
| 2017/0202627 A1 | 7/2017 | Sramek et al. |
| 2017/0209073 A1 | 7/2017 | Sramek et al. |
| 2017/0209217 A1 | 7/2017 | Jensen |
| 2017/0215976 A1 | 8/2017 | Nowlin et al. |
| 2017/0290631 A1 | 10/2017 | Lee et al. |
| 2017/0304021 A1 | 10/2017 | Hathaway |
| 2017/0325906 A1 | 11/2017 | Piecuch et al. |
| 2017/0340353 A1 | 11/2017 | Ahluwalia et al. |
| 2018/0025666 A1 | 1/2018 | Ho et al. |
| 2018/0065252 A1 | 3/2018 | Tabandeh |
| 2018/0078439 A1 | 3/2018 | Cagle et al. |
| 2018/0078440 A1 | 3/2018 | Koenig et al. |
| 2018/0079090 A1 | 3/2018 | Koenig et al. |
| 2018/0104124 A1 | 4/2018 | Revenus et al. |
| 2018/0116758 A1 | 5/2018 | Schlosser |
| 2018/0147105 A1 | 5/2018 | Timm et al. |
| 2018/0177470 A1 | 6/2018 | Suga |
| 2018/0214011 A1 | 8/2018 | Graetzel et al. |
| 2018/0221038 A1 | 8/2018 | Noonan et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0289445 A1 | 10/2018 | Krinninger |
| 2018/0289575 A1* | 10/2018 | Hiratsuka ............ A61G 13/101 |
| 2018/0296285 A1 | 10/2018 | Simi et al. |
| 2018/0325499 A1 | 11/2018 | Landey et al. |
| 2018/0360435 A1 | 12/2018 | Romo |
| 2018/0368920 A1 | 12/2018 | Ummalaneni |
| 2018/0369035 A1* | 12/2018 | Bhimavarapu ........ A61G 7/018 |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0101570 A1* | 4/2019 | Diglio ................. G01R 31/2831 |
| 2019/0110839 A1 | 4/2019 | Rafii-Tari et al. |
| 2019/0151148 A1 | 5/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0255359 A1 | 8/2019 | Benali |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0290523 A1* | 9/2019 | Von Siebenthal ........................... A61G 13/1225 |
| 2019/0298160 A1 | 10/2019 | Ummalaneni et al. |
| 2019/0298458 A1* | 10/2019 | Srinivasan ............ A61B 34/10 |
| 2019/0298460 A1 | 10/2019 | Al-Jadda |
| 2019/0298465 A1* | 10/2019 | Chin ...................... A61B 17/29 |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0374417 A1* | 12/2019 | Hiratsuka ............. A61G 13/06 |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0022767 A1 | 1/2020 | Hiii |
| 2020/0038124 A1* | 2/2020 | Lin ........................ A61B 34/10 |
| 2020/0039086 A1 | 2/2020 | Meyer |
| 2020/0046434 A1 | 2/2020 | Graetzel |
| 2020/0054408 A1 | 2/2020 | Schuh et al. |
| 2020/0060516 A1 | 2/2020 | Baez, Jr. |
| 2020/0093549 A1 | 3/2020 | Chin |
| 2020/0093554 A1 | 3/2020 | Schuh |
| 2020/0100845 A1 | 4/2020 | Julian |
| 2020/0100853 A1* | 4/2020 | Ho ......................... A61B 34/30 |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146789 A1 | 5/2020 | Eyre |
| 2020/0188043 A1 | 6/2020 | Yu |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | Defonzo |
| 2020/0281787 A1 | 9/2020 | Ruiz |
| 2021/0101288 A1* | 4/2021 | Lee .......................... A61G 7/05 |

FOREIGN PATENT DOCUMENTS

| | | |
|---|---|---|
| CN | 104853709 A | 8/2015 |
| EP | 3195842 A1 | 7/2017 |
| GB | G8-810956 A | 3/1959 |
| NL | 9101035 A | 1/1993 |
| WO | WO-2010088005 A2 | 6/2010 |
| WO | 2019076526 A1 | 4/2019 |

OTHER PUBLICATIONS

Notice of Allowance dated May 3, 2022; U.S. Appl. No. 17/202,220, filed Mar. 15, 2021; 9 pages.

European Extended Search Report; Application No. 20769679.0; dated Mar. 2, 2023; 12 pages.

* cited by examiner

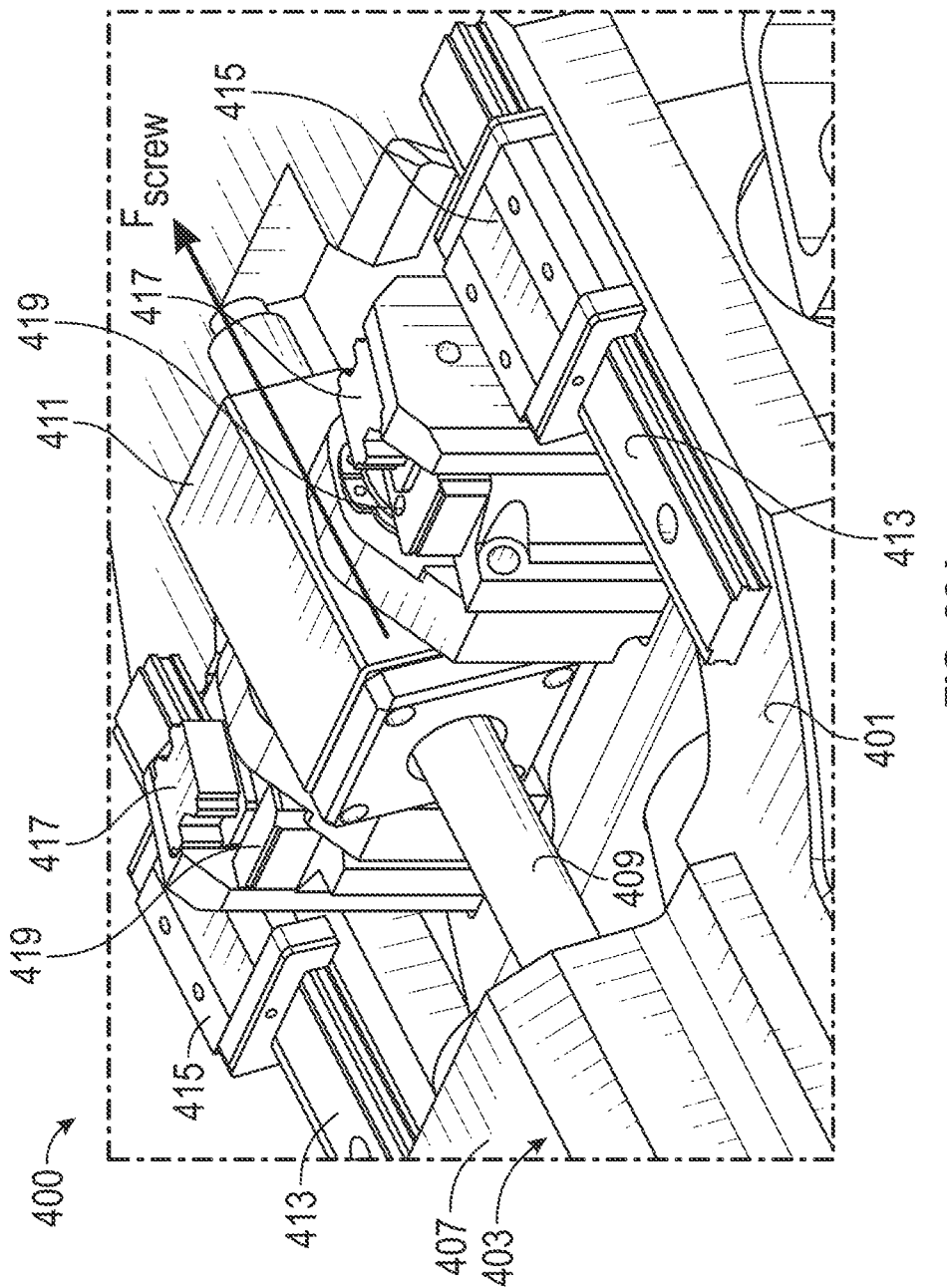

TILT MECHANISMS FOR MEDICAL SYSTEMS AND APPLICATIONS

CROSS-REFERENCE TO RELATED APPLICATIONS

This application is a continuation application of U.S. patent application Ser. No. 17/202,220, filed Mar. 15, 2021, which is a continuation application of U.S. patent application Ser. No. 16/810,469, filed Mar. 5, 2020, now, U.S. Pat. No. 10,945,904, which claims the benefit of, and priority to U.S. Provisional Patent App. No. 62/815,848, filed Mar. 8, 2019, the disclosures of each of which is incorporated by reference herein in its entirety and for all purposes.

TECHNICAL FIELD

This application relates generally to robotic medical systems, and in particular, to tilt mechanisms for patient platforms of robotic medical systems.

BACKGROUND

Patient platforms, such as tables or beds, can be used to support a patient during a medical procedure. For example, patient platforms are often used during manual medical procedures, as well as during robotic medical procedures. Generally, such patient platforms are horizontally oriented.

SUMMARY

A surgical or medical robotics system with robotic arm(s) and a patient platform is configurable to perform a variety of surgical or medical procedures. In a first aspect, a tilt mechanism for a medical platform includes a tilt plate, a linear actuator mounted on the tilt plate and configured to apply a linear force to a pivot housing, and a first linear guide attached to a gimbal. The first linear guide extends along a first axis and the pivot housing is configured to translate along the first linear guide, and application of the linear force to the pivot housing tilts the tilt plate relative to the gimbal by causing the pivot housing to translate along the first linear guide.

The tilt mechanism can include one or more of the following features in any combination: (a) wherein the pivot housing is further configured to pivot relative to the first linear guide as the pivot housing translates along the first linear guide; (b) wherein the linear actuator applies the linear force in a direction along a second axis; (c) wherein the first axis and the second axis are not parallel; (d) wherein the linear actuator comprises a motor that is configured to rotate a lead screw, and the pivot housing comprises a screw nut housing mounted on the lead screw; (e) wherein the tilt plate is configured to pivot relative to the gimbal about a pivot axis, and the pivot axis is configured to translate relative to the gimbal along the first axis; (f) a second linear guide attached to the tilt plate, wherein the first linear guide comprises a first set of rails, and the second linear guide comprises a second set of rails; (g) wherein the first set of rails are positioned between the second set of rails; and/or (h) wherein the tilt plate is attached to a patient platform, and the gimbal is attached to a column that supports the patient platform.

In another aspect, a robotic medical system includes a patient platform configured to support a patient during a medical procedure, a column supporting the patient platform, and a tilt mechanism connecting the column to the patient platform. The tilt mechanism includes a lateral tilt mechanism configured to pivot the patient platform about a lateral tilt axis of the patient platform, and a longitudinal tilt mechanism configured to pivot the patient platform about a longitudinal tilt axis of the patient platform.

The system can include one or more of the following features in any combination: (a) wherein the lateral tilt mechanism and the longitudinal tilt mechanism are configured to be operated simultaneously; (b) wherein the lateral tilt mechanism is positioned on top of the longitudinal tilt mechanism; (c) wherein the lateral tilt mechanism comprises a linear actuator configured to apply a linear force in a direction perpendicular to the lateral tilt axis to pivot the patient platform about the lateral tilt axis; (d) wherein the lateral tilt mechanism comprises a tilt plate attached to the patient platform, a linear actuator mounted on the tilt plate and configured to apply a linear force to a pivot housing, a first linear guide attached to a gimbal, wherein the first linear guide extends along a first axis and the pivot housing is configured to translate along the first linear guide, and a second linear guide attached to the tilt plate, wherein the second linear guide extends along a second axis and the pivot housing is configured to translate along the second linear guide; (e) wherein application of the linear force to the pivot housing tilts the tilt plate relative to the gimbal by causing the pivot housing to translate along the first linear guide and the second linear guide; (f) wherein the linear actuator applies the linear force in a direction that is parallel to the second axis; (g) wherein the first axis and the second axis are not parallel; (h) wherein the linear actuator comprises a motor that is configured to rotate a lead screw, and the pivot housing comprises a screw nut housing mounted on the lead screw; (i) wherein the tilt plate is configured to pivot relative to the gimbal about the lateral tilt axis, and the lateral tilt axis is configured to translate relative to the gimbal along the first axis; (j) wherein the longitudinal tilt mechanism comprises a longitudinal tilt linkage extending between the column and the gimbal, and an actuator configured to actuate the longitudinal tilt linkage to pivot the gimbal relative to the column to cause the patient platform to tilt about the longitudinal tilt axis; (k) wherein the actuator comprises a longitudinal linear actuator configured to translate along an axis of the column to actuate the longitudinal tilt linkage; (L) wherein the lateral tilt mechanism is configured to allow at least 15 degrees of tilt about the lateral tilt axis, and the longitudinal tilt mechanism is configured to allow at least 30 degrees of tilt about the longitudinal tilt axis; and/or (m) wherein the lateral tilt mechanism is configured to allow about 30 degrees of tilt about the lateral tilt axis, and the longitudinal tilt mechanism is configured to allow about 45 degrees of tilt about the longitudinal tilt axis.

In another aspect a method for controlling tilt of a patient platform comprises: tilting the patient platform about a lateral tilt axis based on: actuating a linear actuator to apply a linear force to a pivot housing; translating the pivot housing along a first linear guide along a first axis; and translating the pivot housing along a second linear guide along a second axis.

The method can include one or more of the following features in any combination: (a) wherein the first axis is parallel to the linear force and the second axis is not parallel to the first axis; (b) wherein actuating the linear actuator comprises driving a lead screw with a motor, and wherein the pivot housing comprises a screw nut housing mounted on the lead screw; (c) wherein the motor is attached to a tilt plate that supports the patient platform, and wherein the first linear guide is attached to the tilt plate; (d) wherein the second linear guide is attached to a gimbal; (e) pivoting the gimbal relative to a column that supports the patient platform to tilt the patient platform about a longitudinal tilt axis; (f) wherein pivoting the gimbal relative to a column comprises driving a longitudinal tilt linkage with a longitudinal linear actuator that translates along an axis of the column; (g) tilting the patient platform about the lateral tilt axis and the longitudinal tilt axis simultaneously; and/or (h) performing a robotic medical procedure on a patient supported on the patient platform.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 28A is an isometric view of the lateral tilt mechanism of FIG. 25 illustrating application of a linear force.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
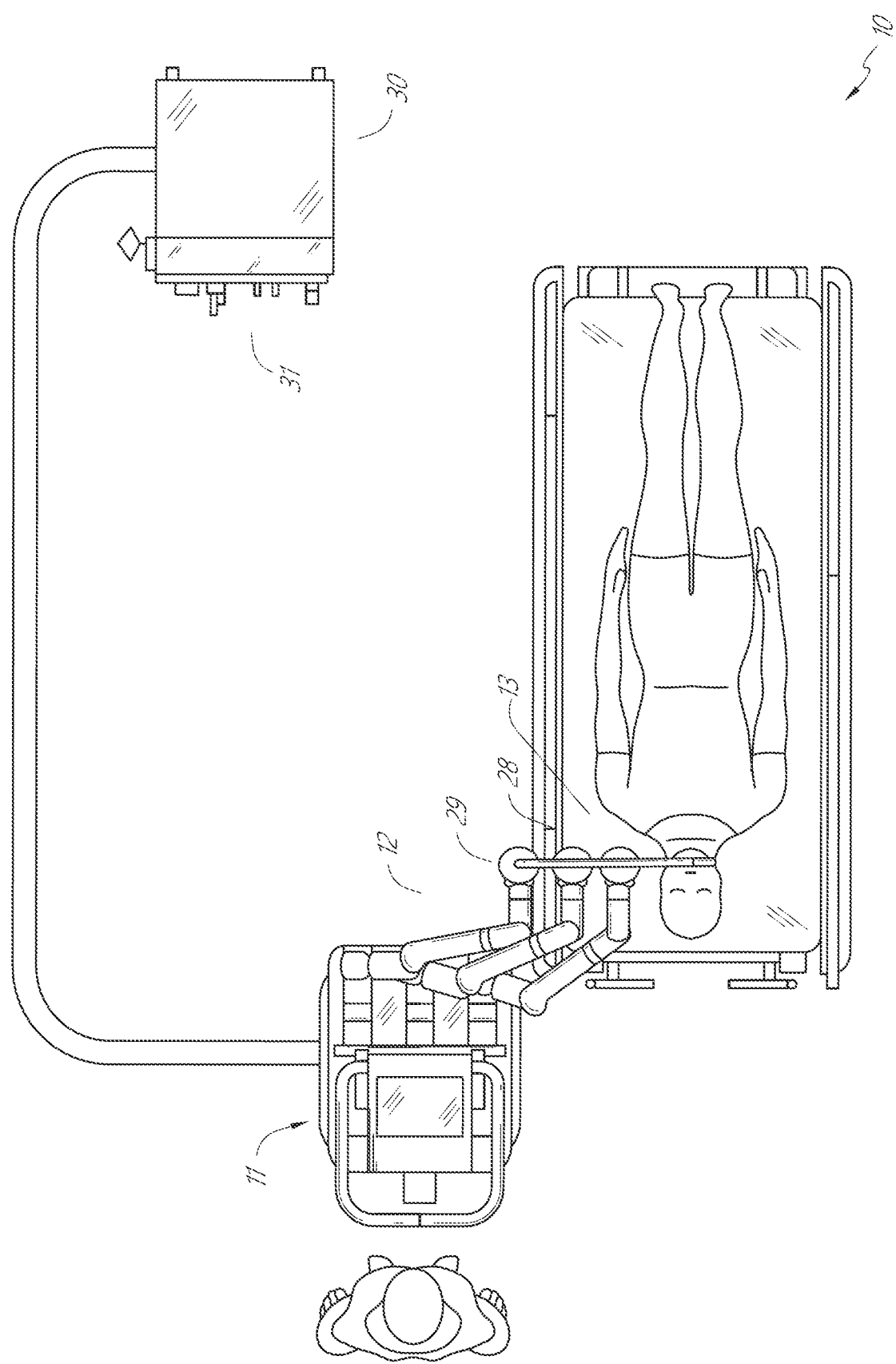
FIG. 1 illustrates an embodiment of a cart-based robotic system arranged for diagnostic and/or therapeutic bronchoscopy.
Figure 2:
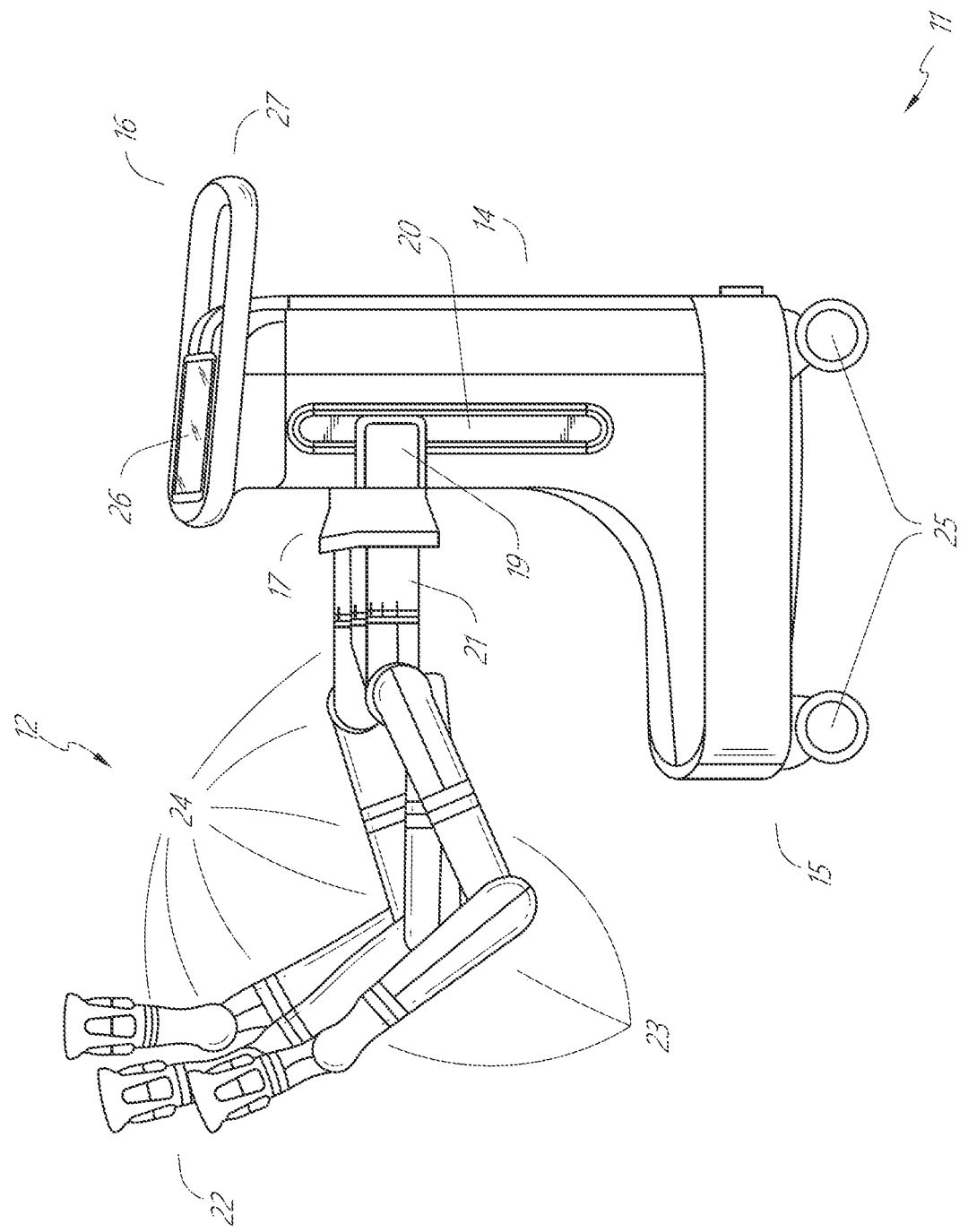
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
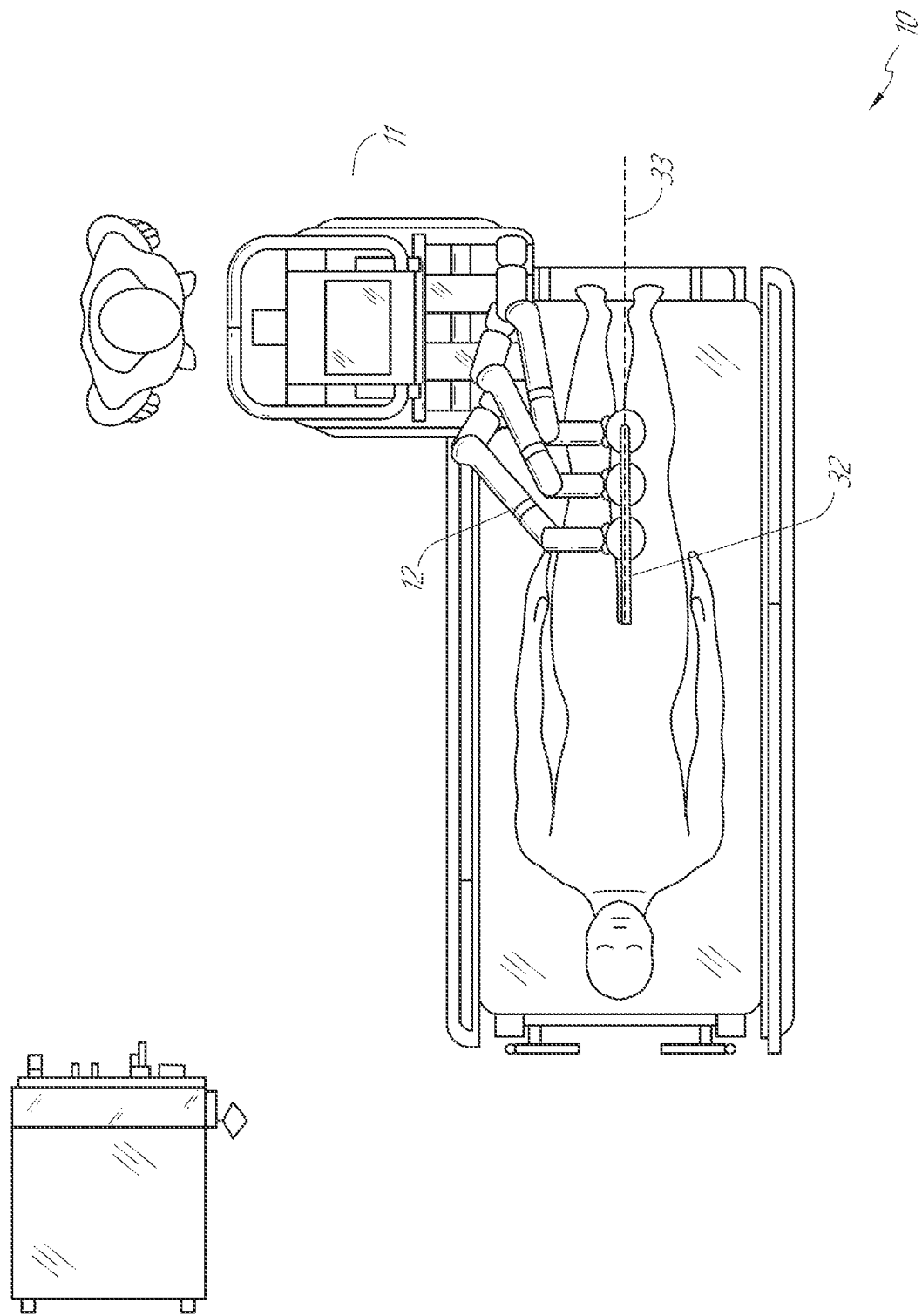
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
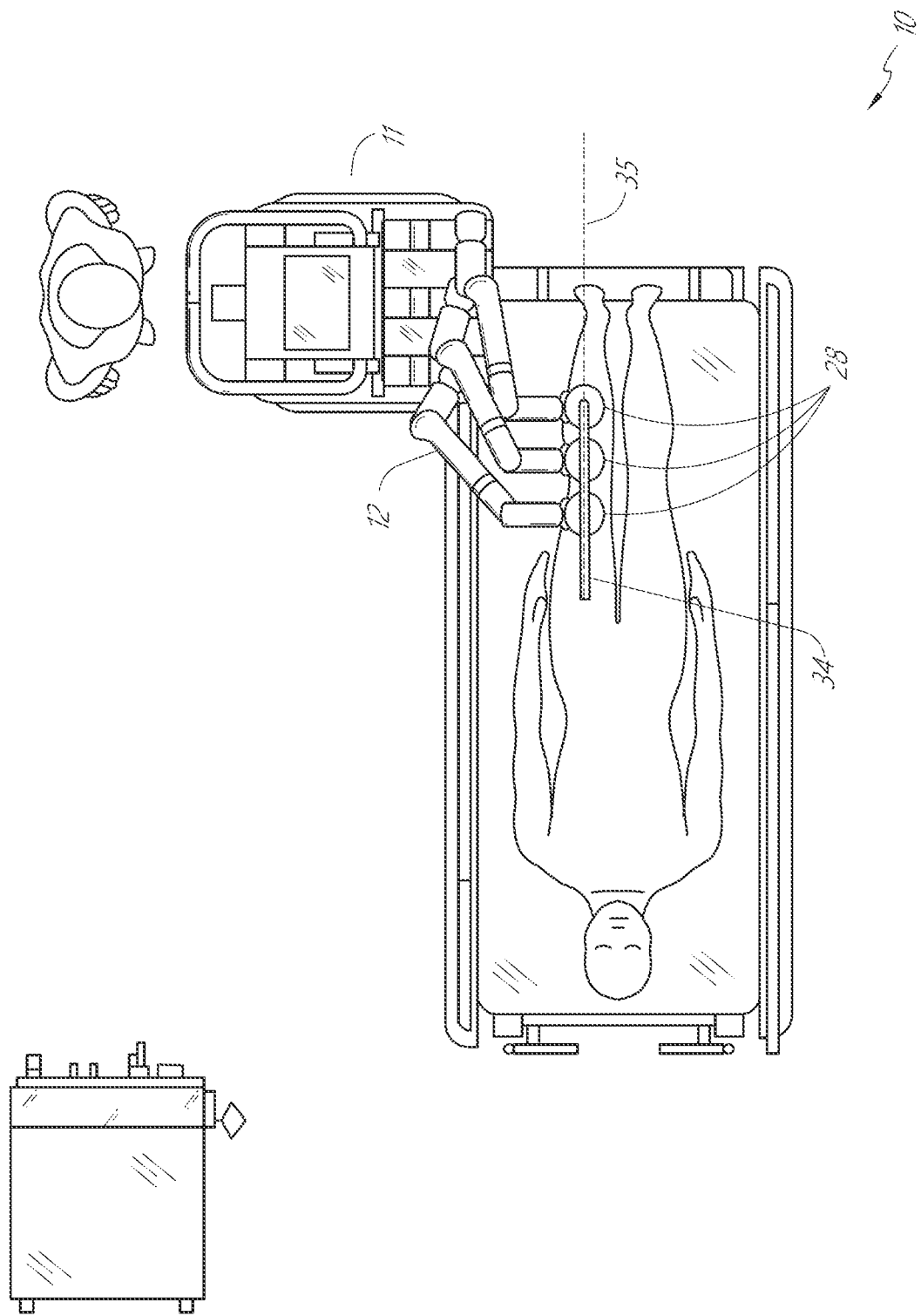
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
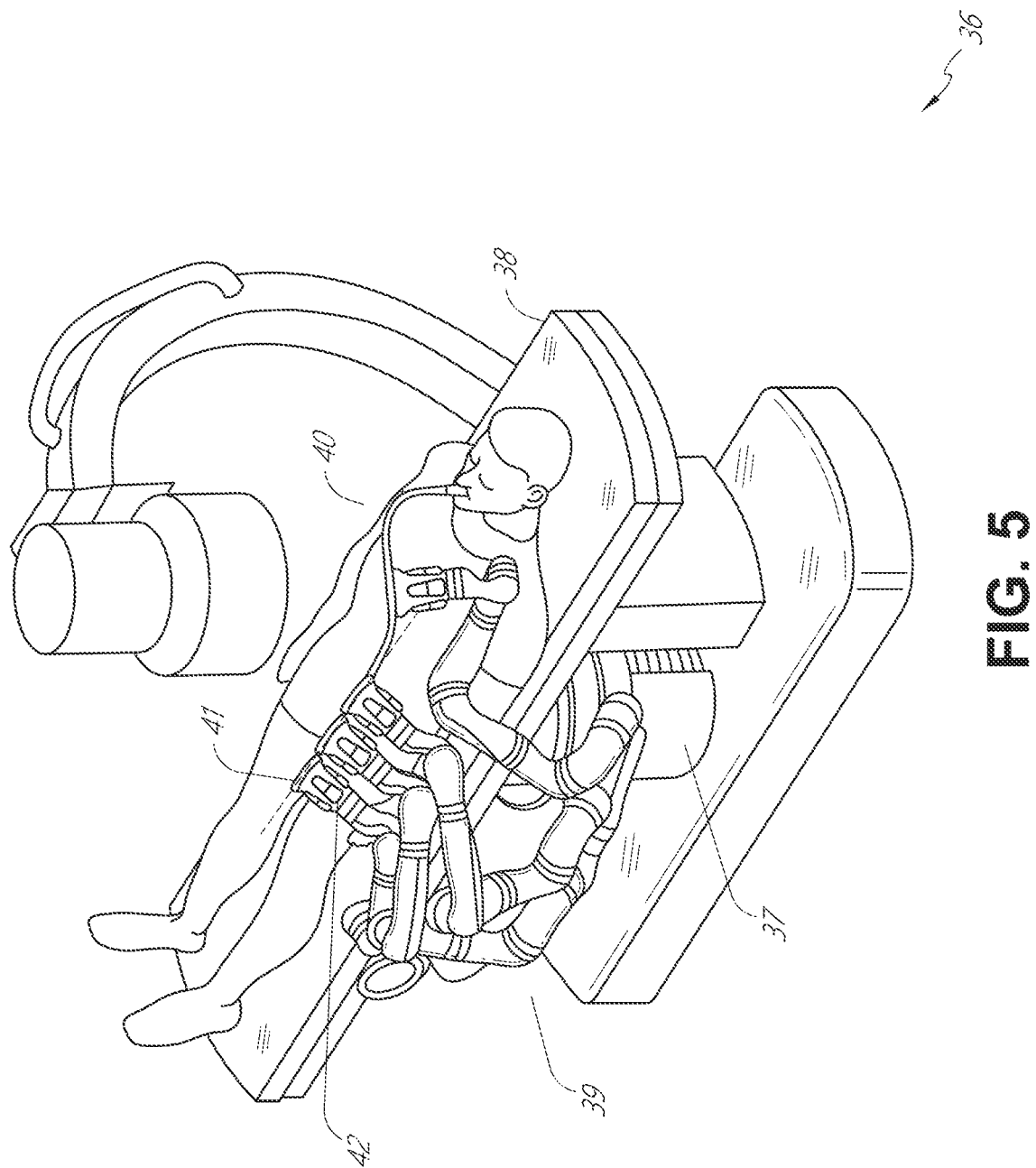
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
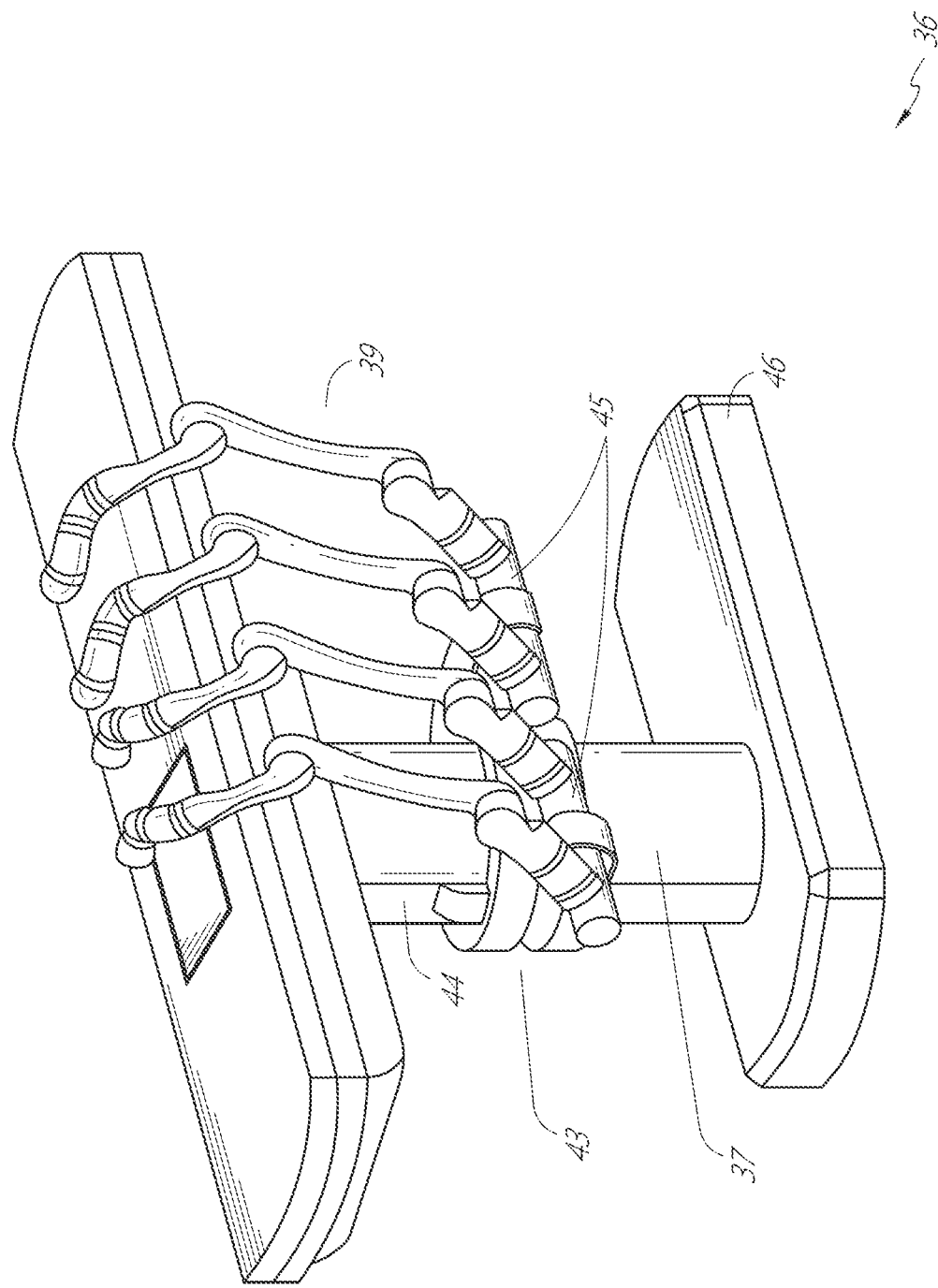
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
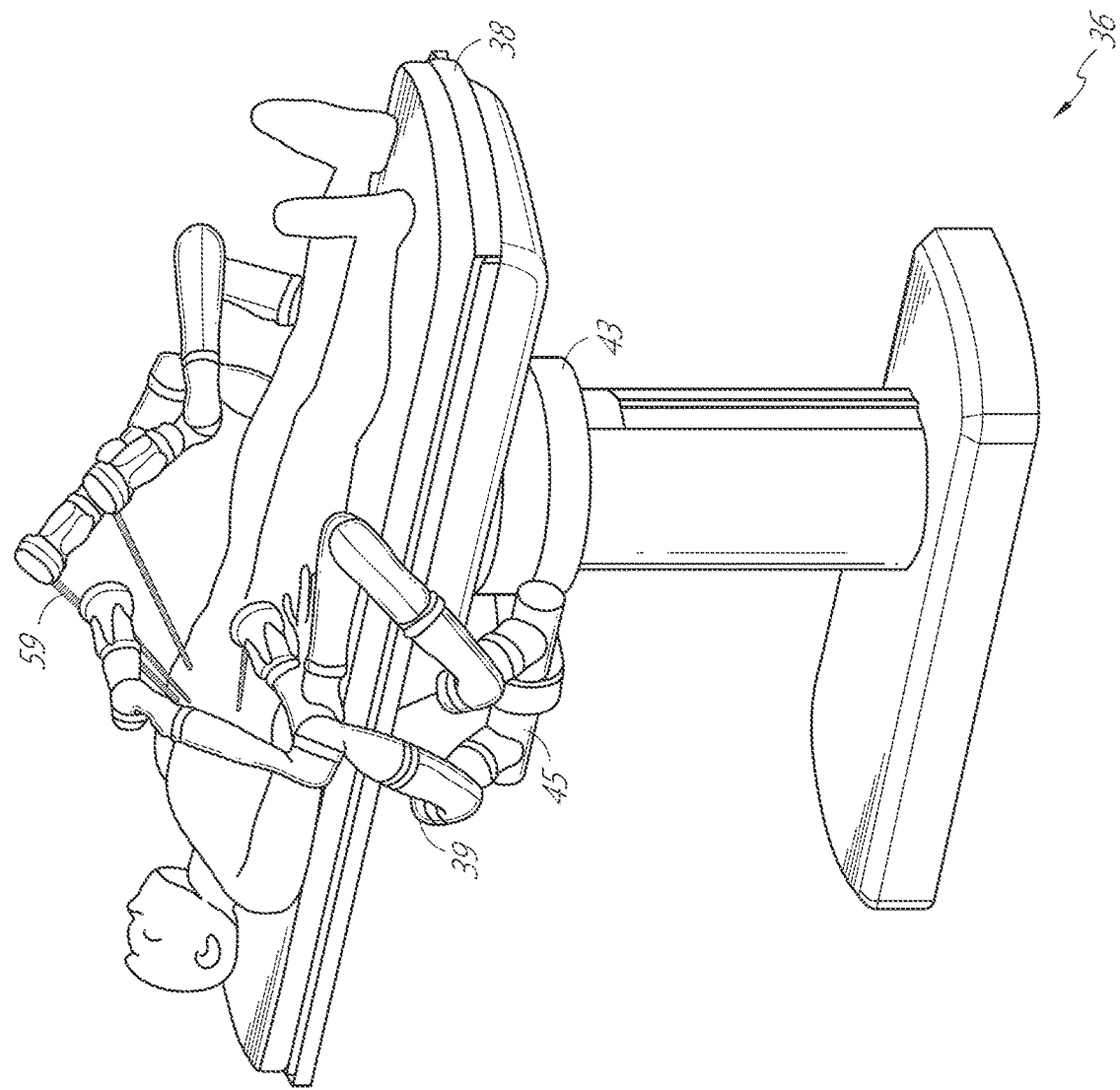
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intra-operative information, such as real-time imaging, navigation, and tracking information. In some embodiments, the tower may also contain holders for gas tanks to be used for insufflation.

Figure 7:
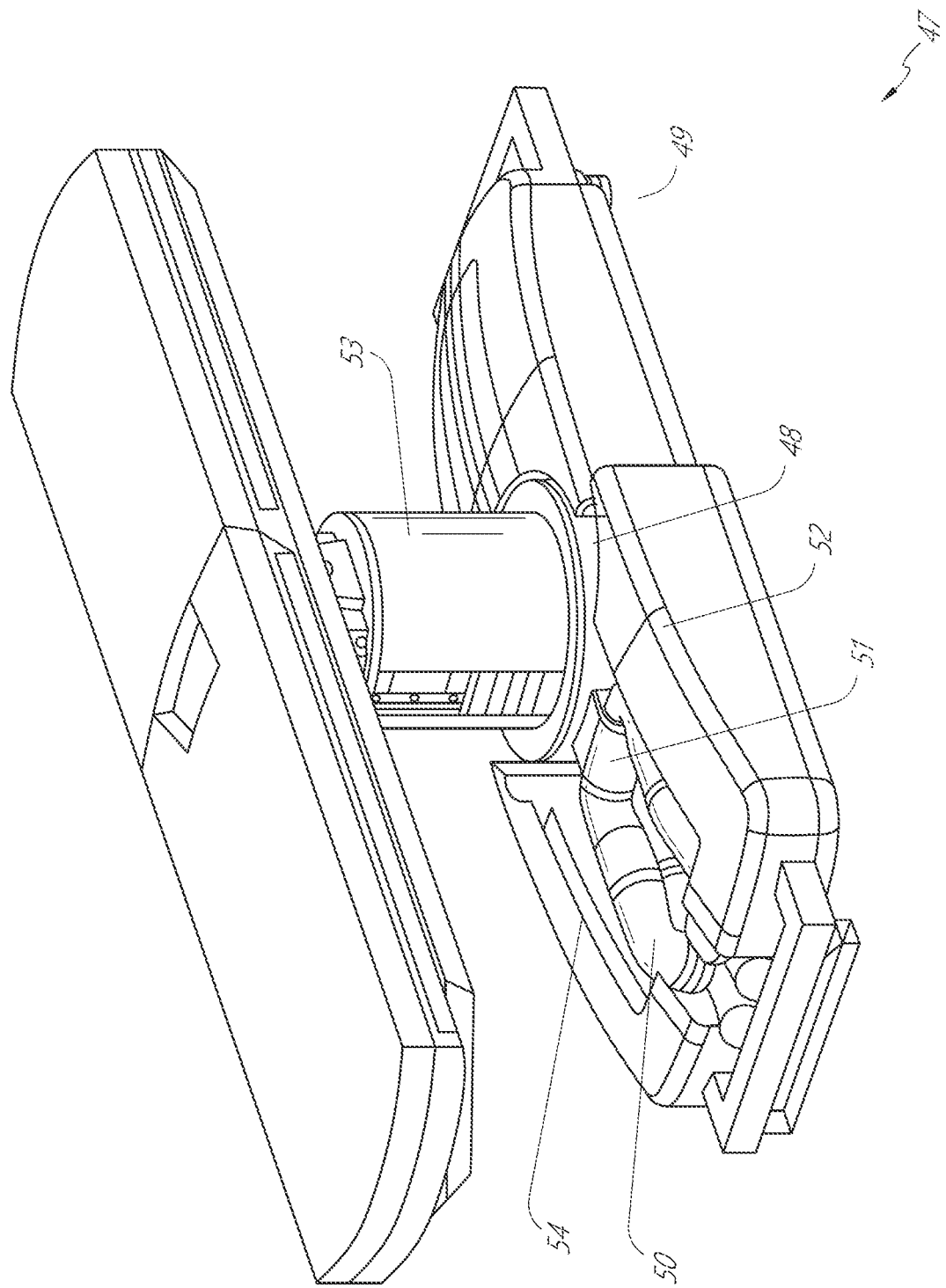
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
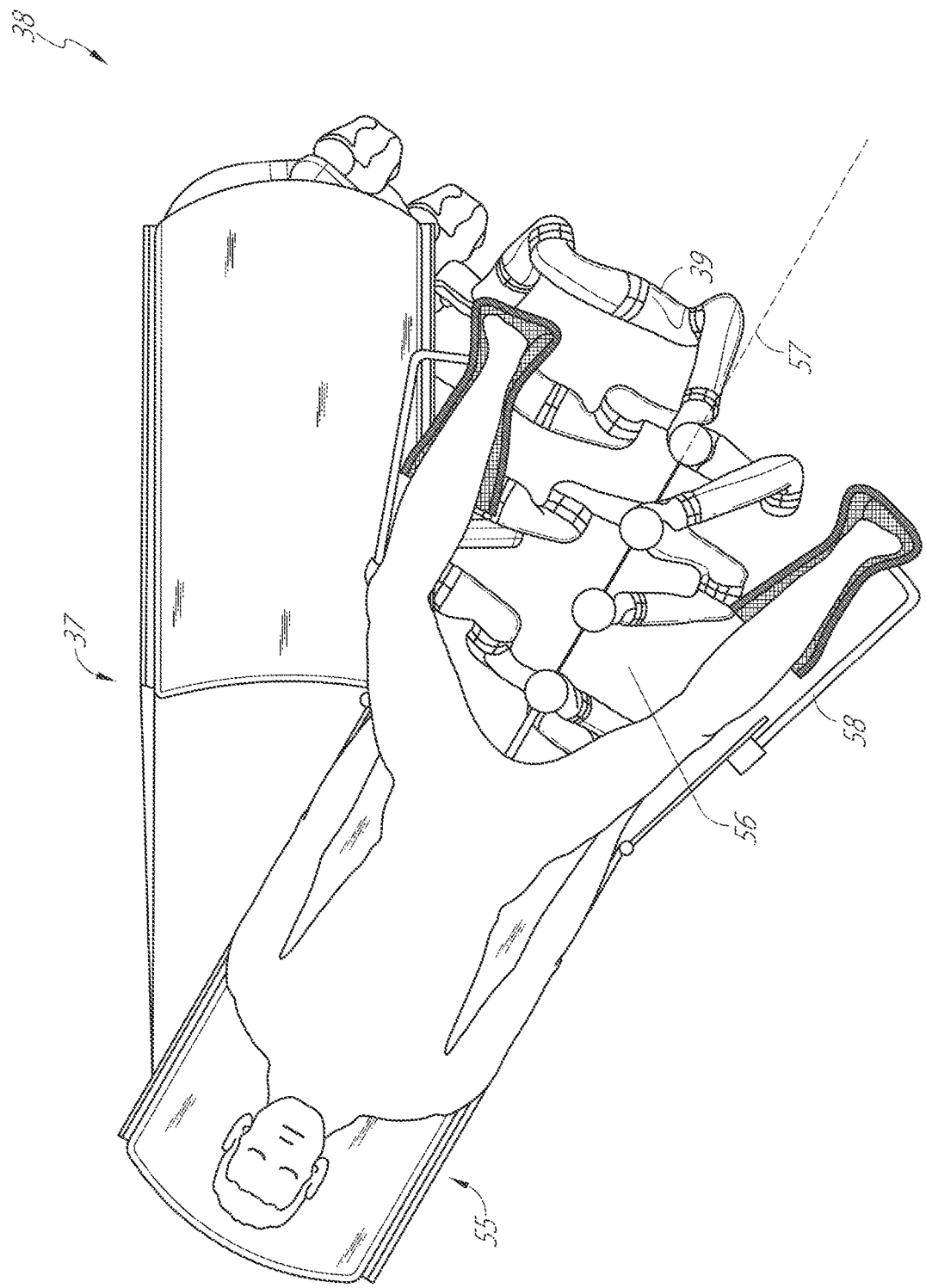
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
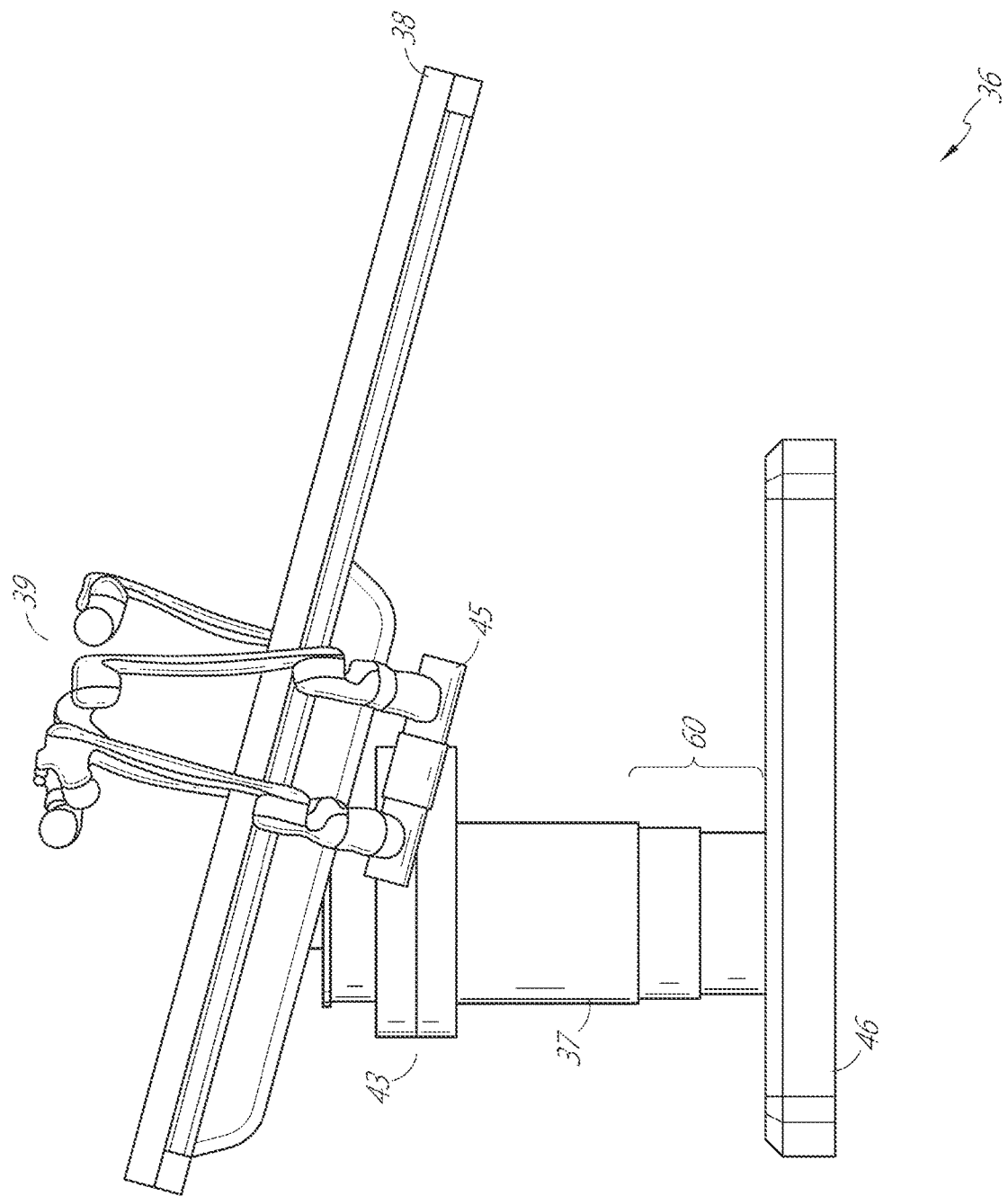
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
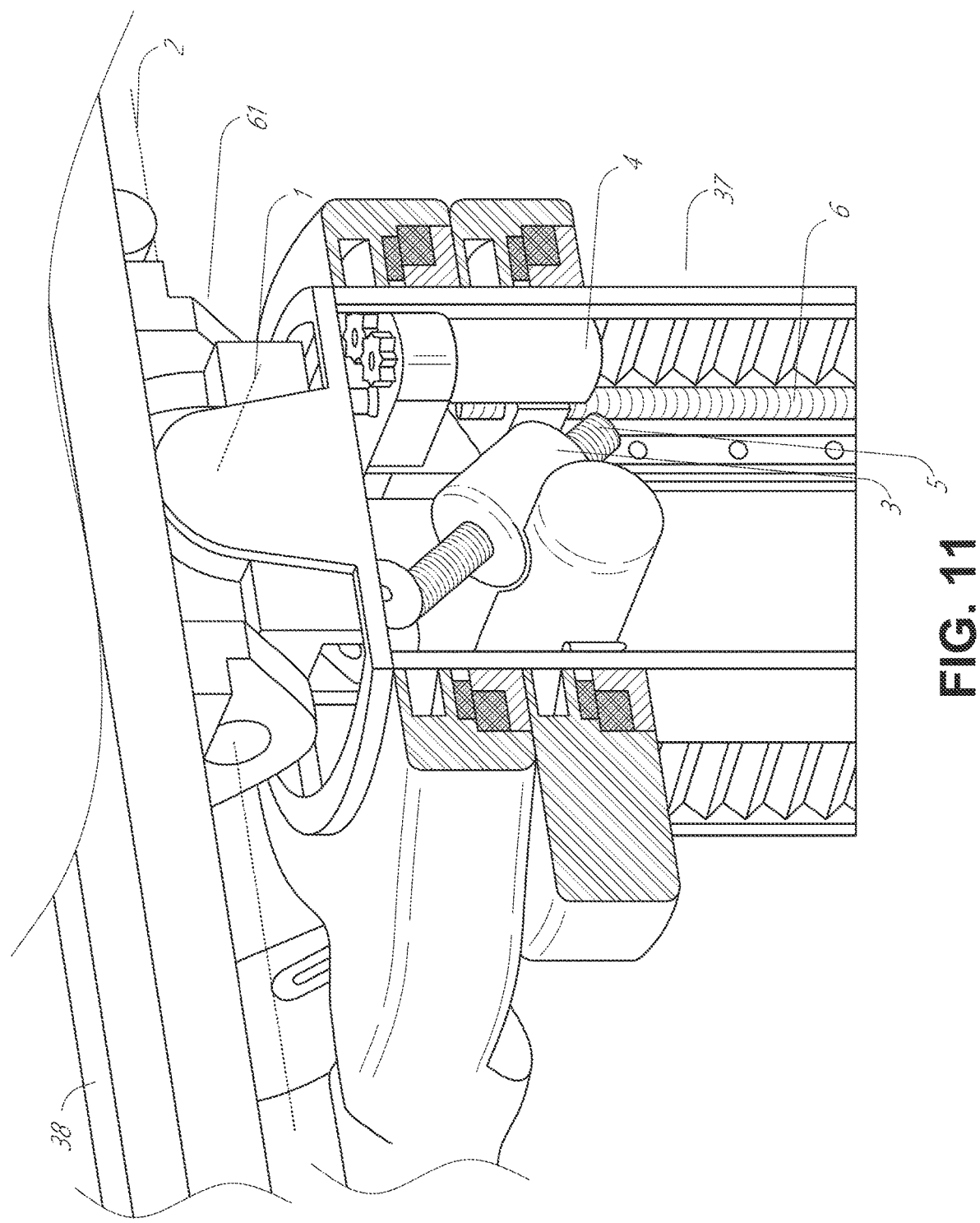
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
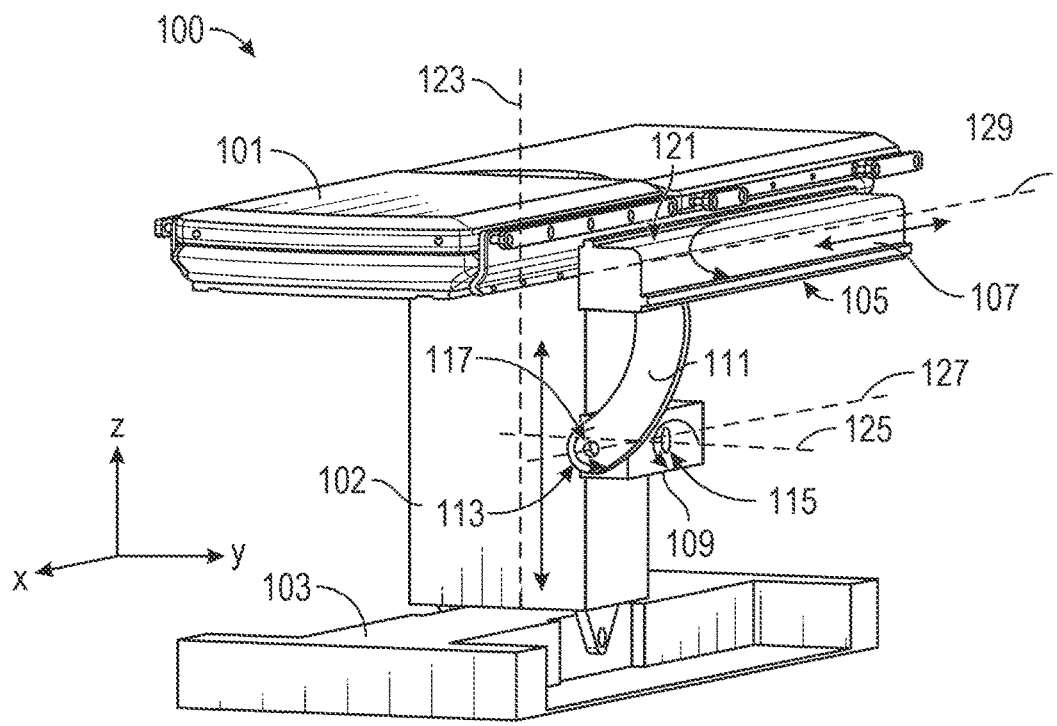
FIG. 12 illustrates an alternative embodiment of a table-based robotic system.
Figure 13:
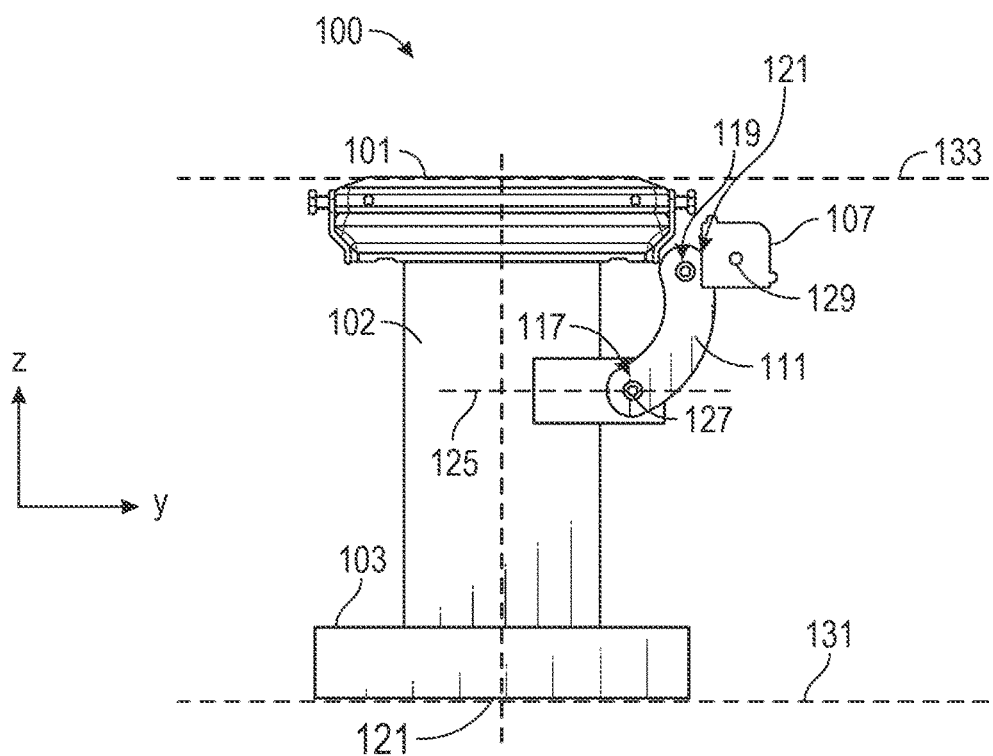
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom (Z-lift) to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
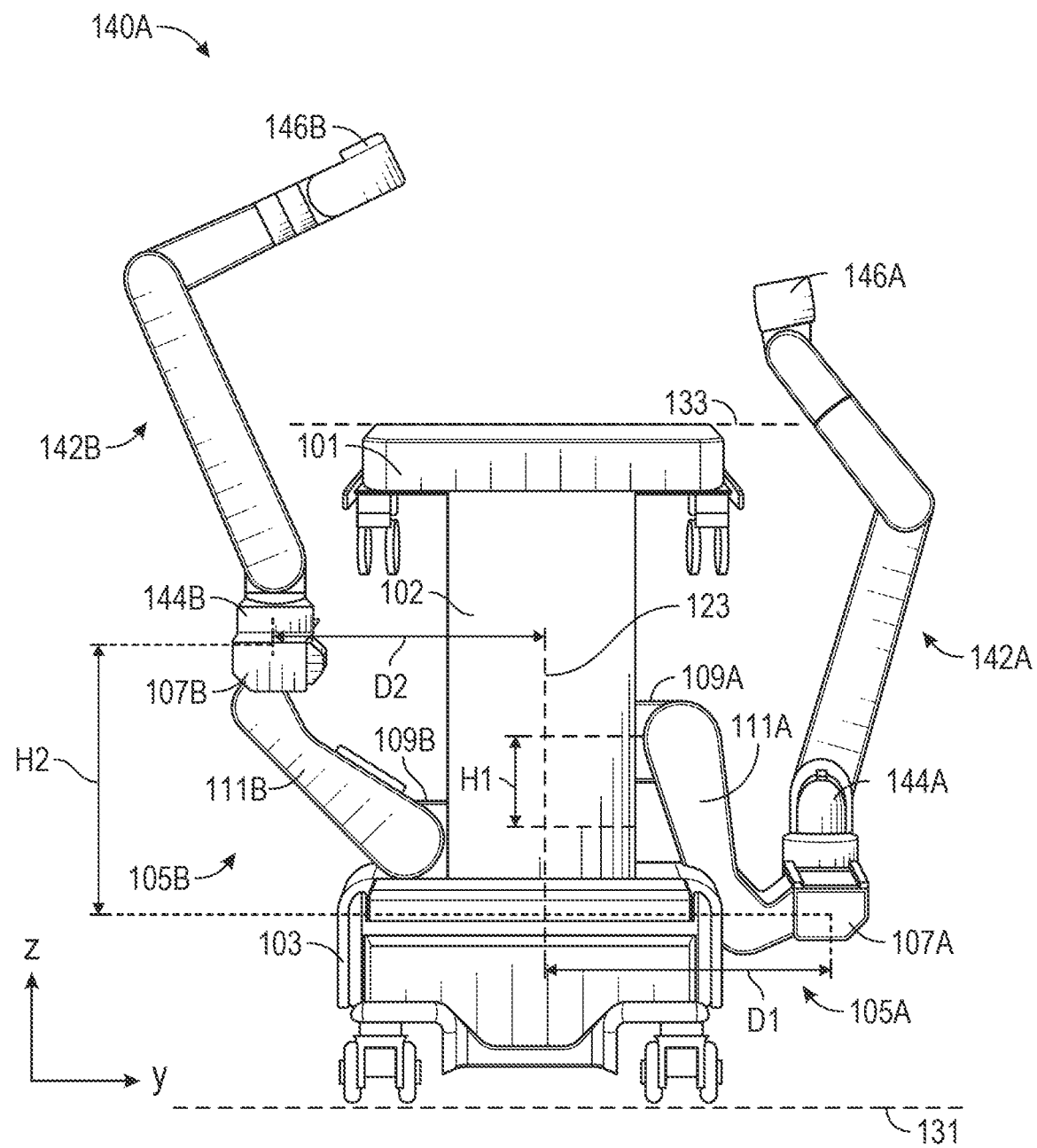
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
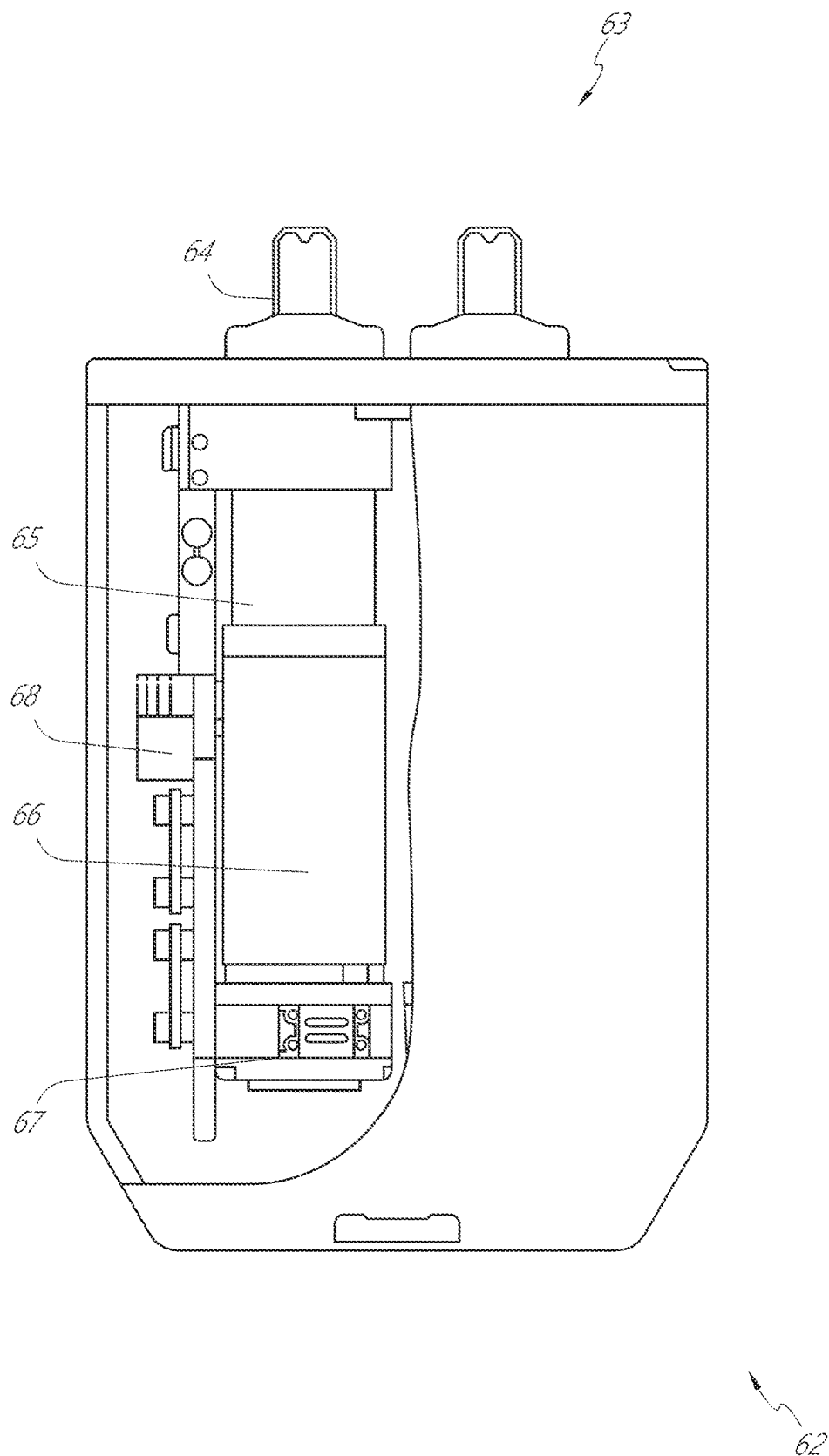
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
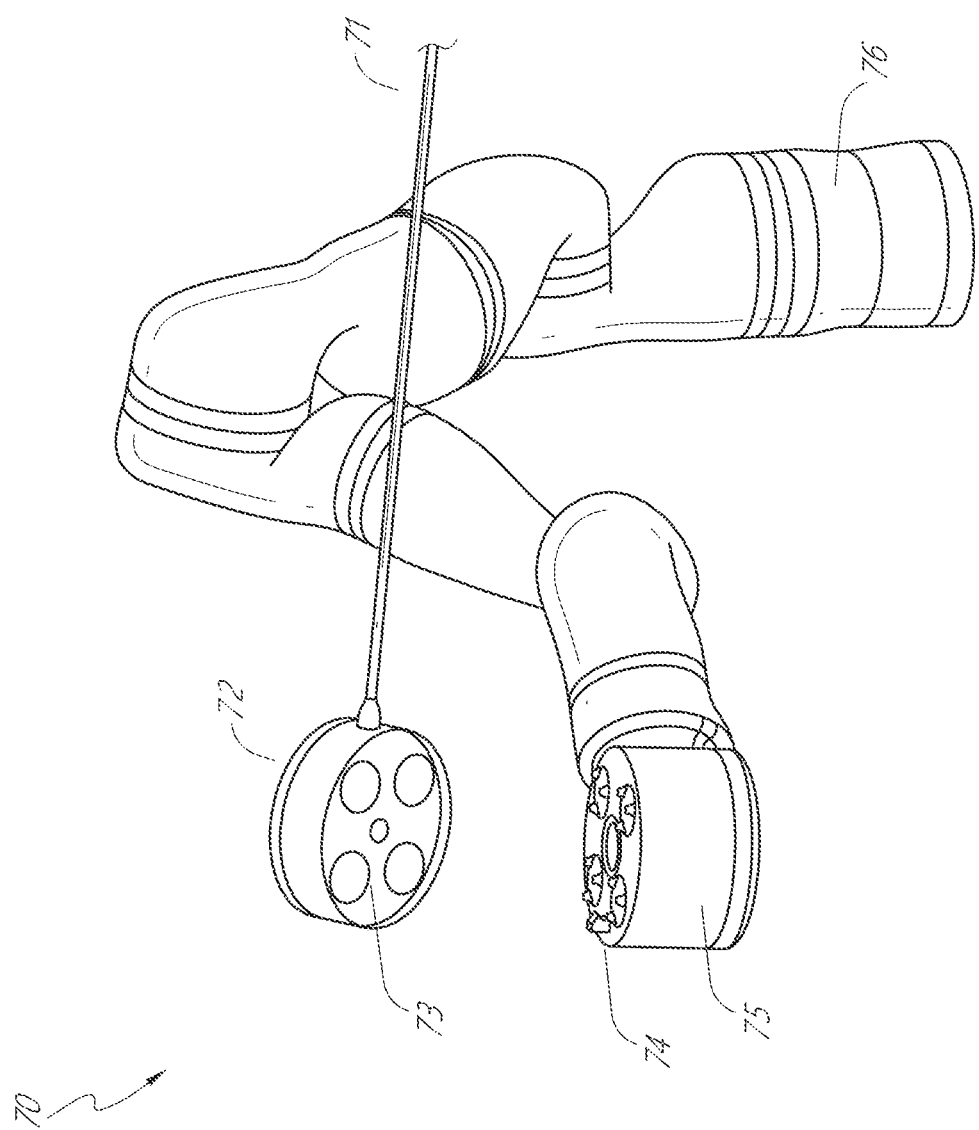
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
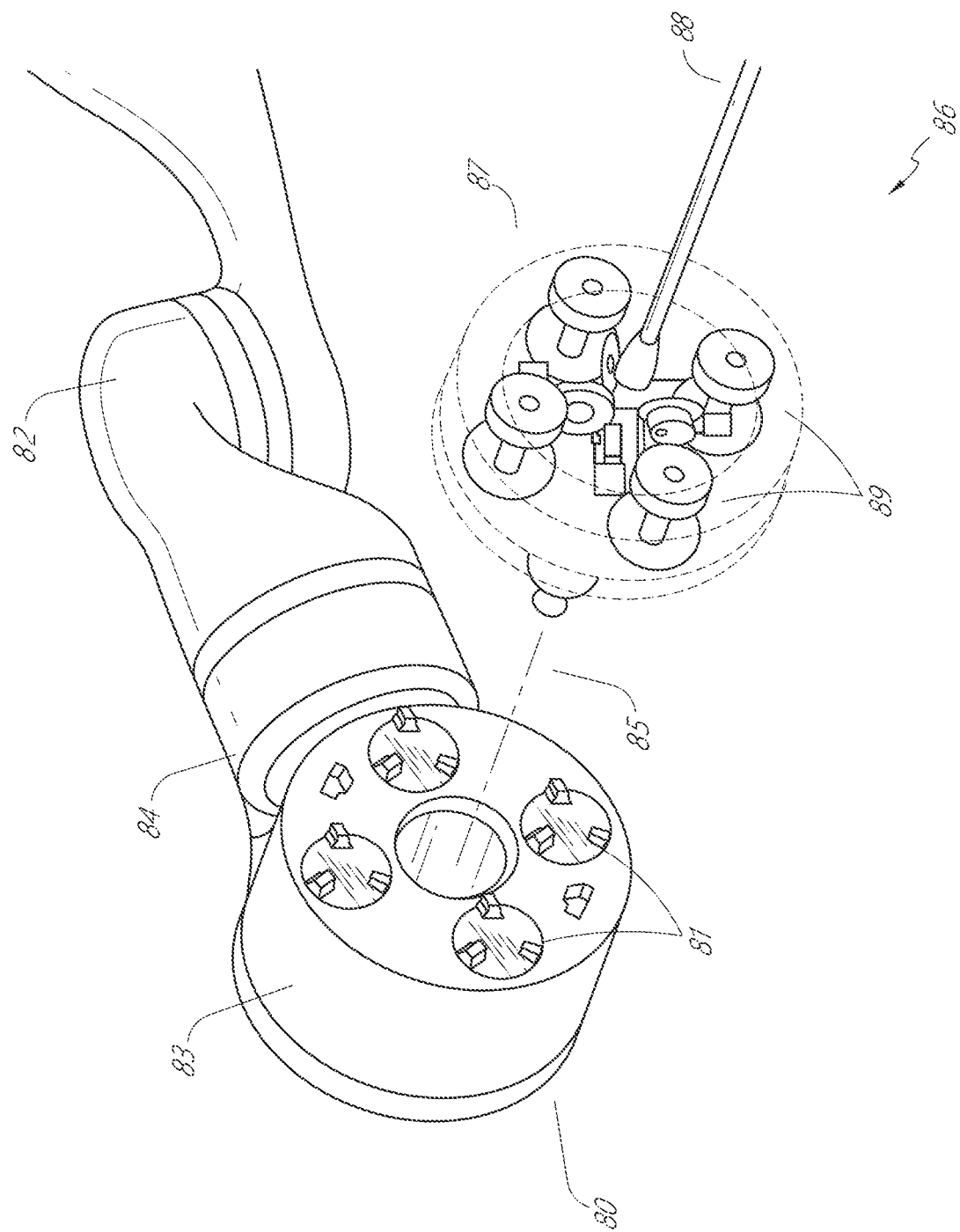
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
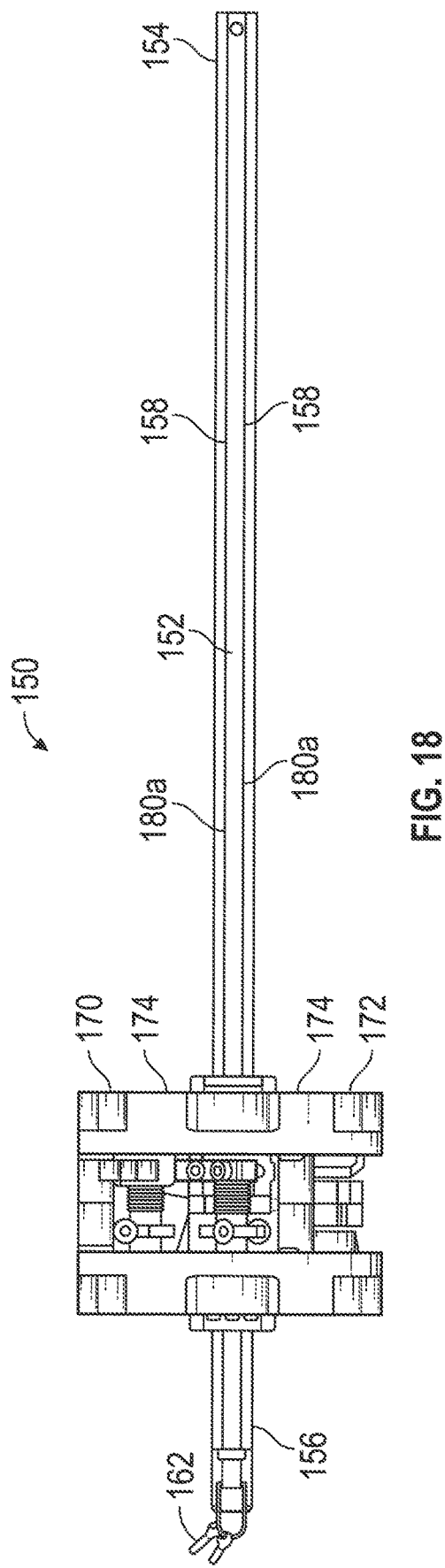
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
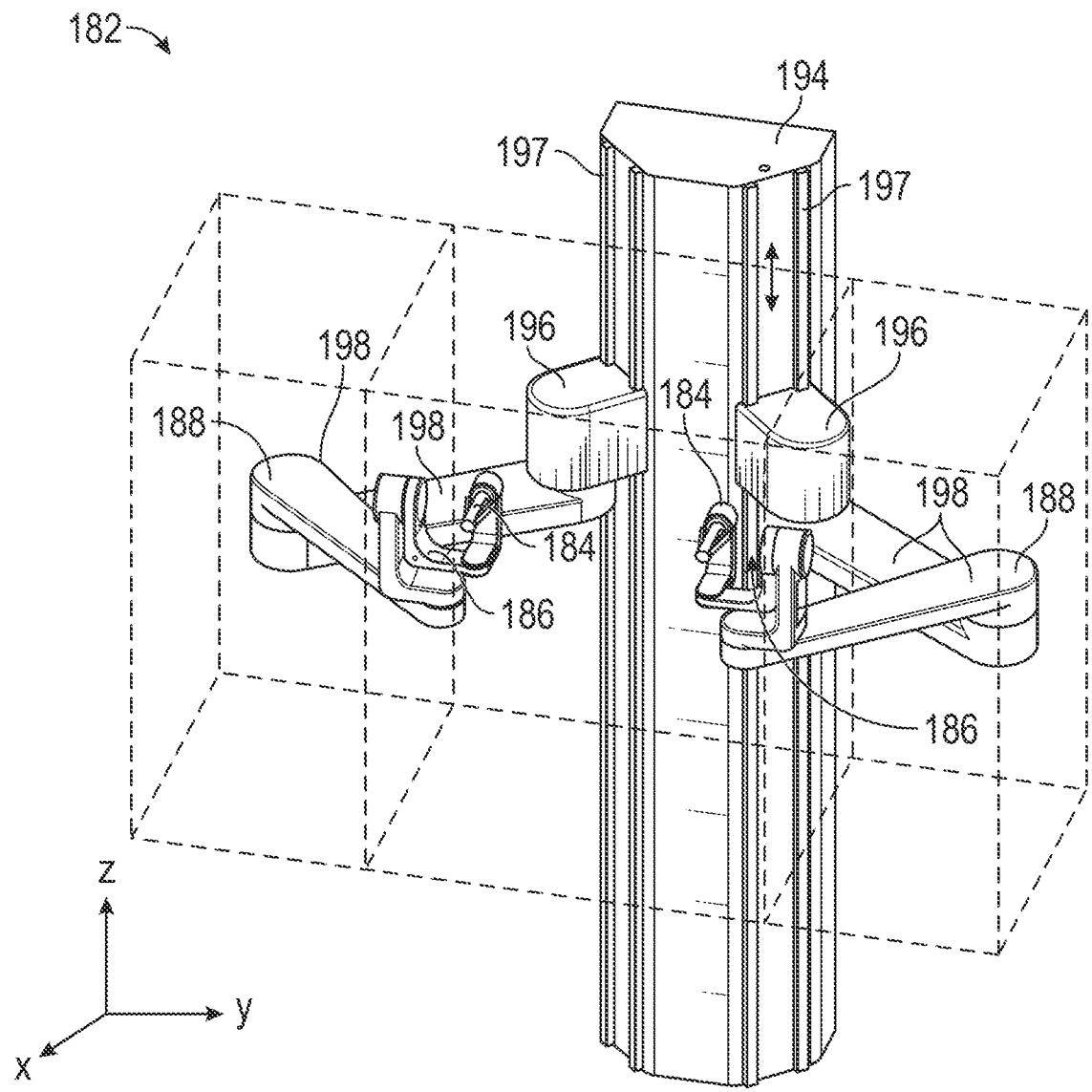
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
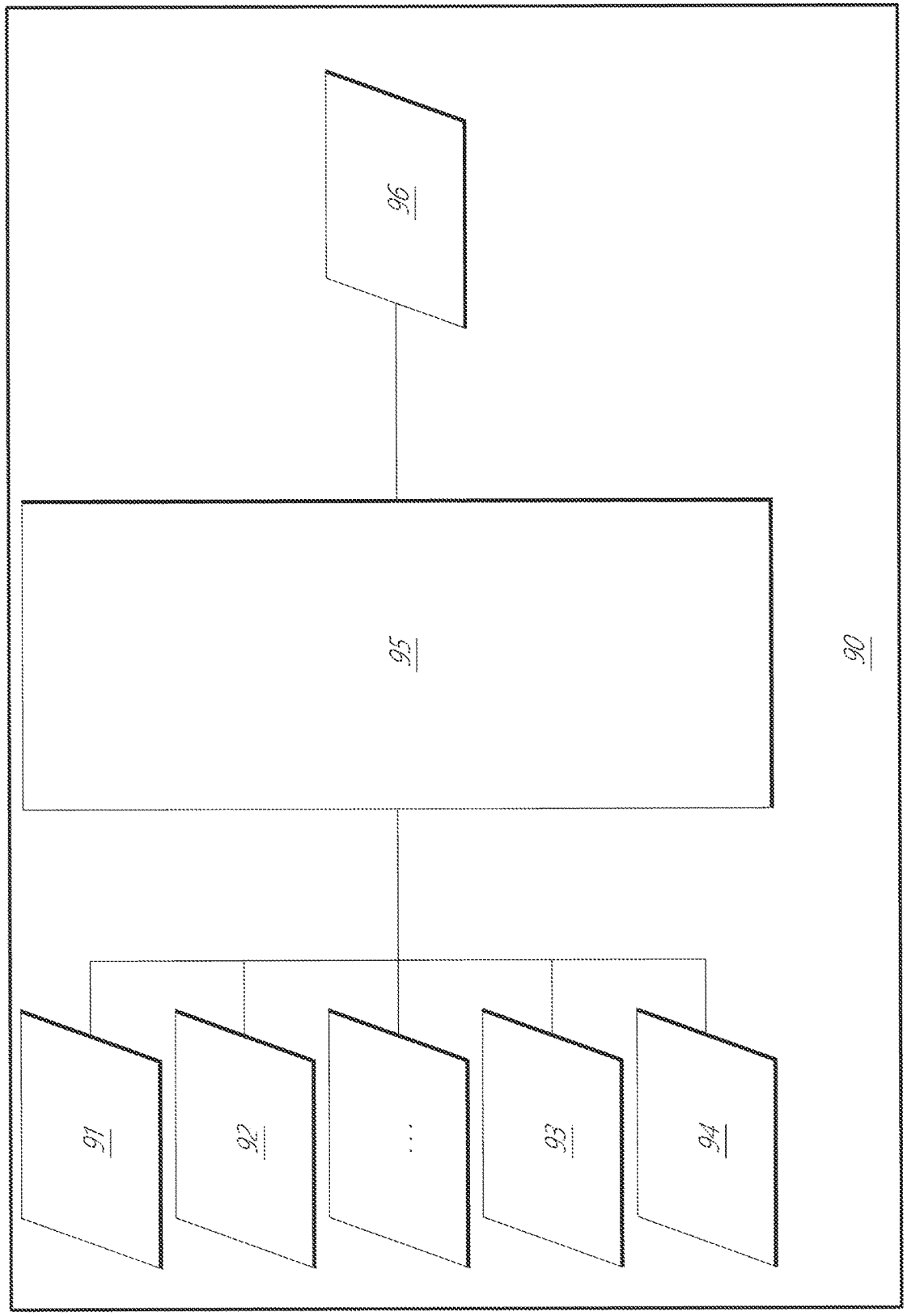
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Tilt Mechanisms for Patient Platforms of Robotic Medical Systems

As shown in several of the examples described above, robotic medical systems can include a patient platform (also referred to as a bed or table). The patient platform can be configured to support a patient during a medical procedure, such as robotic endoscopy, robotic laparoscopy, open procedures, or others (see, for example, FIGS. 1, 3, 4, 5, 8, and 9, described above). Generally, a patient lies on (or is otherwise positioned on) the patient platform during the procedure. The procedure can then be performed using one or more robotic arms and one or more robotically controllable medical instruments that have access to the patient positioned on the patient platform. Patient platforms are also used in many non-robotic (i.e., manual) medical procedures.

In some embodiments, the patient platform comprises a generally horizontal surface for supporting the patient. That is, in some embodiments, the patient platform comprises a surface for supporting the patient that is generally parallel to a surface that supports the patient platform (e.g., the ground or floor).

During some medical procedures, however, it may be beneficial to position the patient platform at other positions (e.g., non-horizontal positions) or angles (e.g., angles that are not parallel to the surface or floor that supports the patient platform). More specifically, for some medical procedures it may be desirable to pivot, rotate, or tilt the patient platform laterally (side-to-side) or longitudinally (head-to-toe) relative to the horizontal or default position. In some instances, it may be beneficial to tilt the patient platform simultaneously in both lateral and longitudinal directions.

For example, during a cholecystectomy procedure, a physician may desire to tilt the patient platform laterally. This can be done to allow access to a gallbladder.

Tilting the patient platform longitudinally may place a patient positioned on the patient platform in a Trendelenburg position (with the patient's feet elevated above the head) or a reverse Trendelenburg position (with the patient's head elevated above the feet). As one example, during a hysterectomy procedure, a physician may desire to tilt the patient platform longitudinally. This can be done to allow access to the uterus.

During a Roux-en-Y gastric bypass (RYGB) procedure, simultaneous lateral and longitudinal tilt may be desired in order to access the target anatomy. The medical procedures listed here provide examples during which lateral and/or longitudinal tilt may be desirable or beneficial. This list is not exhaustive, and lateral and/or longitudinal tilt may be beneficially used during many other medical procedures. Further, while the examples provided illustrate application to robotic medical procedures, lateral and/or longitudinal tilt may also be beneficially implemented in non-robotic or manual medical procedures, as well as generally endoscopic and/or percutaneous procedures.

This application is directed to novel tilt mechanisms for patient platforms. The tilt mechanisms can be configured to provide lateral and/or longitudinal tilt. In some embodiments, the tilt mechanisms are configured for use with robotic medical systems, such as those described above with reference to FIGS. 1-20 and others. This need not be the case in all embodiments, however, and the tilt mechanisms for patient platforms described herein can also be configured for use with non-robotic or manual medical systems. In some embodiments, the tilt mechanisms are advantageously configured to have a low-profile. The low-profile of the tilt mechanisms can allow the tilt mechanism to fit within a small form factor, while still providing sufficient range of motion as described above and herein. Further, in some embodiments, the tilt mechanism described herein can advantageously be configured to allow both lateral tilt and longitudinal tilt simultaneously.

Figure 21A:
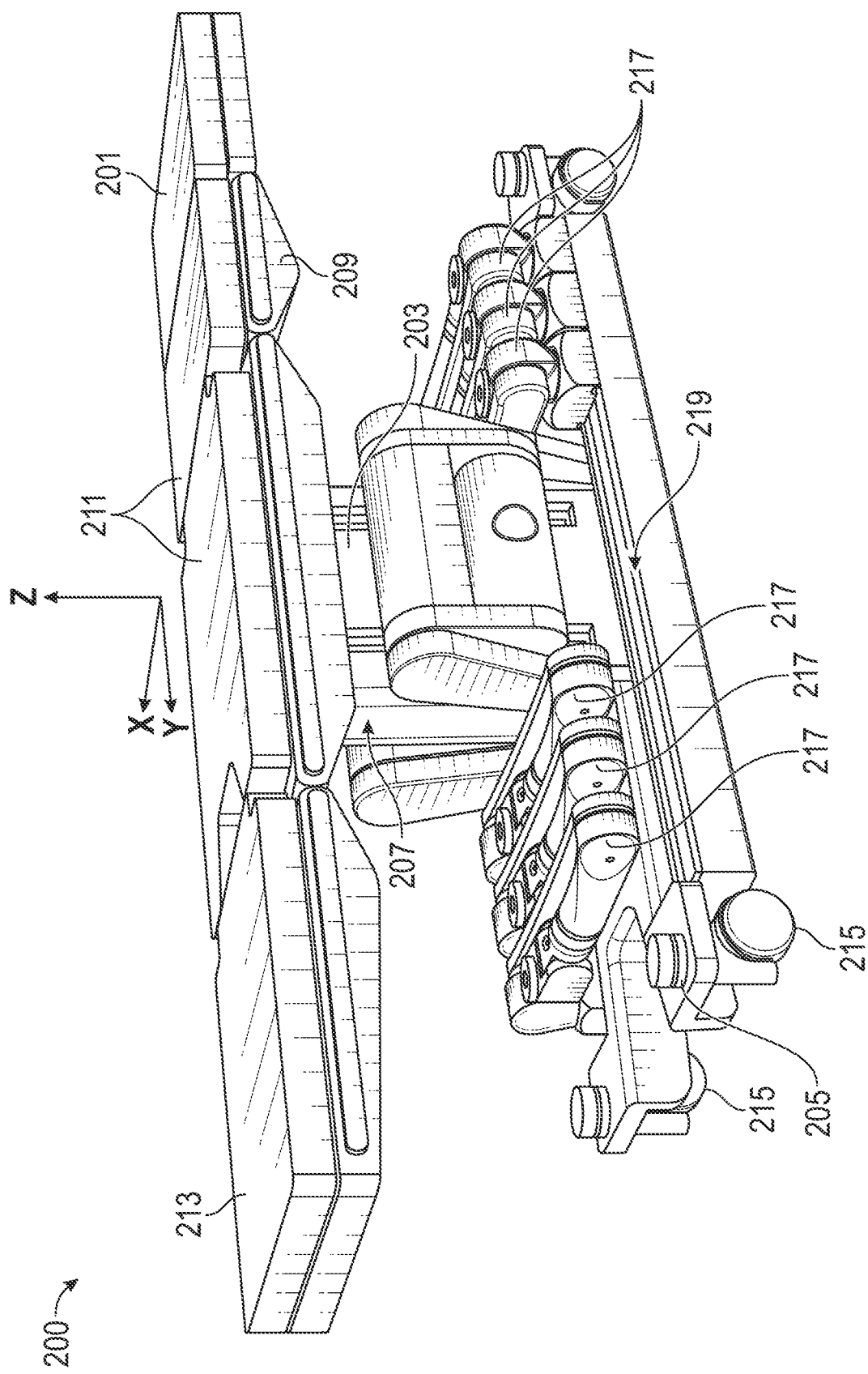
FIG. 21A illustrates an embodiment of a robotic medical system that includes a patient platform in a first configuration.
Figure 21B:
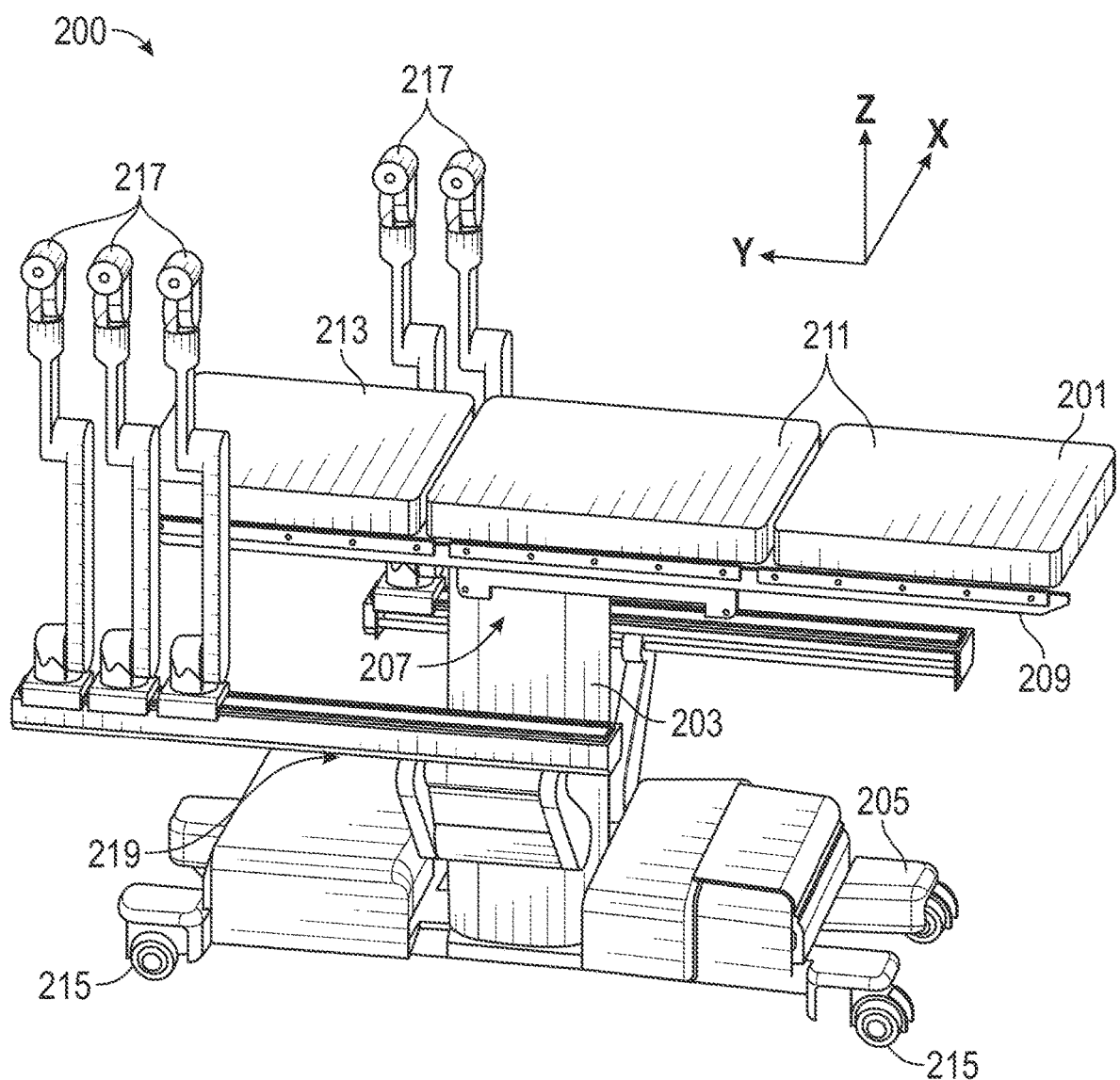
FIG. 21B illustrates the robotic medical system that includes a patient platform of FIG. 21A in a second configuration.
Figure 22A:
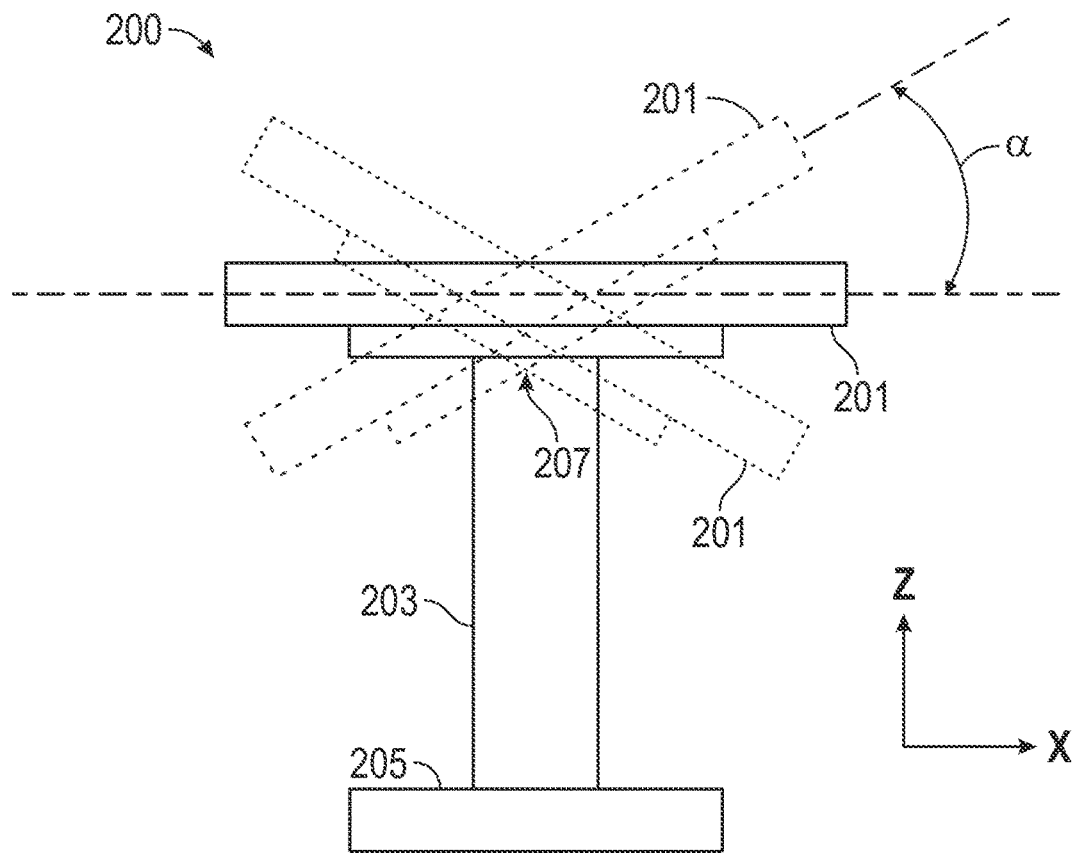
FIG. 22A is an end view of an embodiment of a patient platform of a robotic medical system and illustrates lateral tilt of the patient platform.
Figure 22B:
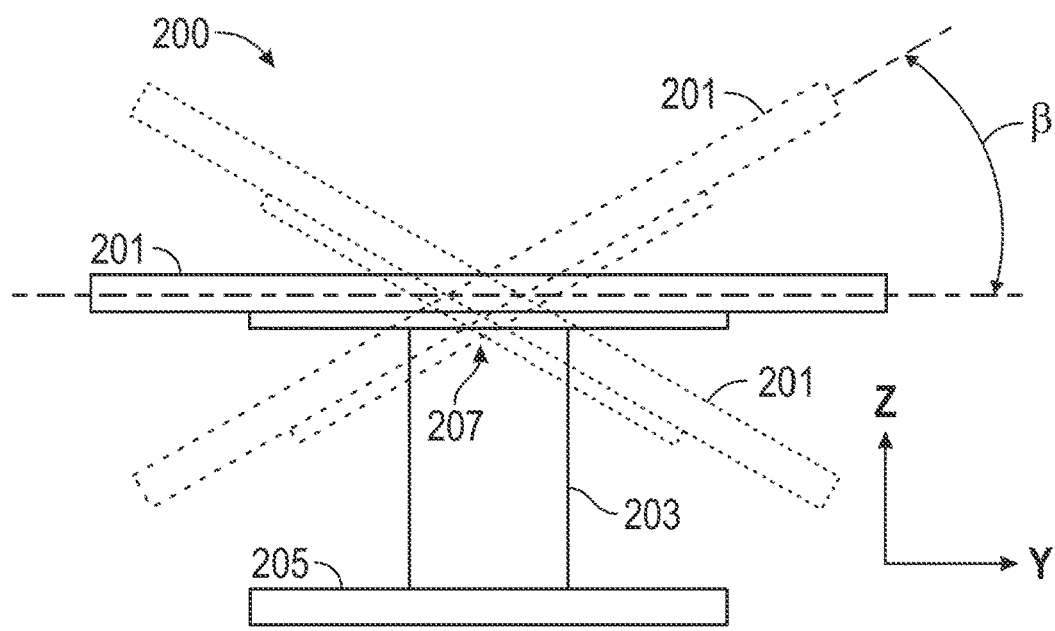
FIG. 22B is a side view of the patient platform of the robotic medical system of FIG. 22A and illustrates longitudinal tilt of the patient platform.

FIGS. 21A and 21B illustrate an embodiment of a robotic medical system 200 that includes a patient platform 201 and a tilt mechanism 207. In this example, the patient platform 201 is supported by a column 203 that extends between a base 205 and the patient platform 201. The tilt mechanism 207 can be positioned between the column 203 and the patient platform 201 to allow the patient platform to pivot, rotate, or tilt relative to the column 203. The tilt mechanism 207 is not shown in great detail in FIGS. 21A and 21B, but several example tilt mechanisms will be described in more detail below with reference to FIGS. 24A-33E. As will be described below, the tilt mechanism 207 can be configured to allow for lateral and/or longitudinal tilt of the patient platform 201. In some embodiments, the tilt mechanism 207 allows for simultaneous lateral and longitudinal tilt of the patient platform 201. FIGS. 21A and 21B show the patient platform 201 in an untilted state or position. In some embodiments, the untilted state or position may be a default position of the patient platform 201. In some embodiments, the default position of the patient platform 201 is a substantially horizontal position as shown. As illustrated, in the untilted state, the patient platform 201 can be positioned horizontally or parallel to a surface that supports the robotic medical system 200 (e.g., the ground or floor). FIGS. 22A and 22B illustrate examples of lateral and longitudinal tilt, respectively, and will be described below.

With continued reference to FIGS. 21A and 21B, in the illustrated example of the system 200, the patient platform 201 comprises a rigid support structure or frame 209. The frame 209 can support one or more surfaces, pads, or cushions 211. An upper surface of the patient platform 201 can comprise a support surface 213. During a medical procedure, a patient can be placed on the support surface 213. The base 205 can be configured to support the system 200. In the illustrated embodiment, the base 205 includes wheels 215. The wheels 215 can allow the system 200 to be easily movable or repositionable. In some embodiments, the wheels 215 are omitted, and the base 205 can rest directly on the ground or floor. In some embodiments, the wheels 215 are replaced with feet.

FIGS. 21A and 21B illustrate that, in some embodiments, the system 200 can include one or more robotic arms 217. The robotic arms 217 can be configured to perform robotic medical procedures as described above with reference to FIGS. 1-20. In some embodiments, one or more robotically-controllable instruments (not shown in FIGS. 21A and 21B) can be coupled to the robotic arms 217 as described above. As shown in FIGS. 21A and 21B, in some embodiments, the robotic arms 217 can be supported on adjustable arm supports 219. The adjustable arm supports 219 can be configured to position one or more of the robotic arms 217 for a robotic medical procedure or to position one or more of the robotic arms 217 for stowage. FIG. 21A illustrates the robotic arms 217 and adjustable arm supports 219 in a stowed configuration below the patient platform 201 and proximal to the base 205. FIG. 21B illustrates the robotic arms 217 and adjustable arm supports 219 in an example deployed configuration where, for example, the robotic arms 217 reach above the patient platform 201. In some embodiments, due to the configuration of the system 200, which enables stowage of different components beneath the patient platform 201 (see FIG. 21A), the robotic arms 217 and the arm supports 219 can occupy a space underneath the patient platform 201. Thus, in some embodiments, it may be advantageous to configure the tilt mechanism 207 to have a low-profile and/or low volume to maximize the space available for storage below the patient platform 201 as described below.

FIGS. 21A and 21B illustrate an example, x, y, and z coordinate system that will be used to describe certain features of the embodiments disclosed herein. It will be appreciated that this coordinate system is provided for purposes of example and explanation only and that other coordinate systems may be used. In the illustrated example, the x-direction or x-axis extends in a lateral direction across the patient platform 201 when the patient platform 201 is in an untilted state. That is, the x-direction extends across the patient platform 201 from one lateral side (e.g., the right side) to the other lateral side (e.g., the left side) when the patient platform 201 is in an untilted state. The y-direction or y-axis extends in a longitudinal direction along the patient platform 201 when the patient platform 201 is in an untilted state. That is, the y-direction extends along the patient platform 201 from one longitudinal end (e.g., the head end) to the other longitudinal end (e.g., the foot end) when the patient platform 201 is in an untilted state. In an untilted state, the patient platform 201 can lie in or be parallel to the x-y plane, which can be parallel to the floor or ground. In the illustrated example, the z-direction or z-axis extends along the column 203 in a vertical direction. As described below with reference to FIGS. 22A and 22B, in some embodiments, the tilt mechanism 207 is configured to laterally tilt the patient platform 201 by rotating the patient platform 201 about a lateral tilt axis that is parallel to the y-axis. The tilt mechanism 207 can further be configured to longitudinally tilt the patient platform 201 by rotating the patient platform 201 about a longitudinal tilt axis that is parallel to the x-axis.

FIG. 22A is an end view of an embodiment of the robotic medical system 200 that illustrates lateral tilt of the patient platform 201. As before, the medical system 200 includes the patient platform 201, which is supported above the base 205 by a column 203. The tilt mechanism 207 can be positioned between the patient platform 201 and the column 203 to allow the patient platform 201 to tilt relative to the column 203. FIG. 22A illustrates an end view, with the y-axis extending into the page. The patient platform 201 is illustrated in three different positions. The patient platform 201 is illustrated in solid lines in an untilted state. The patient platform 201 is illustrated in dashed lines in a first laterally tilted state. In the first laterally tilted state, the patient platform 201 is shown tilted to a lateral tilt angle .alpha. In some embodiments, the tilt mechanism 207 can be configured to allow at least a lateral tilt angle .alpha. of about 5 degrees, 10 degrees, 15 degrees, 20 degrees, 25 degrees, 30 degrees, 35 degrees, 40 degrees, 45 degrees or more relative to the untilted state. In some embodiments, the tilt mechanism 207 can be configured to allow the patient platform 201 to tilt in both lateral directions from the untilted state. That is the lateral tilt angle .alpha. can be positive or negative. A second laterally tilted state with a negative angle .alpha. is illustrated in dotted lines. In some embodiments, the patient platform 201 can be laterally tilted to any angle between the positions illustrated in dashed and dotted lines. As shown in FIG. 22A, lateral tilt can involve pivoting or tilting the patient platform 201 about a lateral tilt axis. The lateral tilt axis can be parallel to the y-axis. For example, in FIG. 22A, the lateral tilt axis extends into and out of the page.

FIG. 22B is a side view of an embodiment of the robotic medical system 200 that illustrates longitudinal tilt of the patient platform 201. In FIG. 22B, the x-axis extends into the page. FIG. 22B illustrates the patient platform 201 in three different positions. The patient platform 201 is illustrated in solid lines in an untilted state. The patient platform 201 is illustrated in dashed lines in a first longitudinally tilted state. In the first longitudinally tilted state, the patient platform 201 is shown tilted to a longitudinal tilt angle .beta. In some embodiments, the tilt mechanism 207 can be configured to allow at least a longitudinal tilt angle .beta. of about 5 degrees, 10 degrees, 15 degrees, 20 degrees, 25 degrees, 30 degrees, 35 degrees, 40 degrees, 45 degrees, 50 degrees, 55 degrees, 60 degrees or more relative to the untilted state (shown in solid lines). In some embodiments, the tilt mechanism 207 can be configured to allow the patient platform 201 to tilt in both longitudinal directions from the untilted state. That is the longitudinal tilt angle .beta. can be positive or negative. A second longitudinally tilted state with a negative angle .beta. is illustrated in dotted lines. In some embodiments, the patient platform 201 can be longitudinally tilted to any angle between the positions illustrated in dashed and dotted lines. As shown in FIG. 22B, longitudinal tilt can involve pivoting or tilting the patient platform 201 about a longitudinal tilt axis. The longitudinal tilt axis can be parallel to the x-axis. For example, in FIG. 22B, the longitudinal tilt axis extends into and out of the page.

As noted previously, in some embodiments, the tilt mechanism 207 is configured to allow simultaneous lateral tilt (FIG. 22A) and longitudinal tilt (FIG. 22B). For example, in some embodiments, the tilt mechanism 207 is configured to allow at least a lateral tilt angle .alpha. of about 15 degrees, 20 degrees, 25 degrees, 30 degrees, 35 degrees, 40 degrees, 45 degrees or more relative to the untilted state while simultaneously allowing at least a longitudinal tilt angle .beta. of about 15 degrees, 20 degrees, 25 degrees, 30 degrees, 35 degrees, 40 degrees, 45 degrees, 50 degrees, 55 degrees, 60 degrees or more relative to the untilted state. In some embodiments, to achieve simultaneous lateral and longitudinal tilt, the tilt mechanism 207 may comprise a lateral tilt mechanism and a longitudinal tilt mechanism that can be operated simultaneously. An example lateral tilt mechanism 400 will be described below with reference to FIGS. 24A-29, and an example tilt mechanism 500 that includes the lateral tilt mechanism 400 and a longitudinal tilt mechanism 510 will be describe with reference to FIGS. 30A-31. Another tilt mechanism 700 that is configured to provide both lateral and longitudinal tilt is shown in FIGS. 33A-33E.

In some embodiments, the tilt mechanism 207 is configured to support a significant load in order to support patients of various sizes, as well as the weight of the patient platform 201 itself. In some embodiments, the tilt mechanism 207 is configured to accommodate at least 300 pounds, at least 400 pounds, at least 500 pounds, at least 600 pounds, at least 700 pounds or more.

Figure 23:
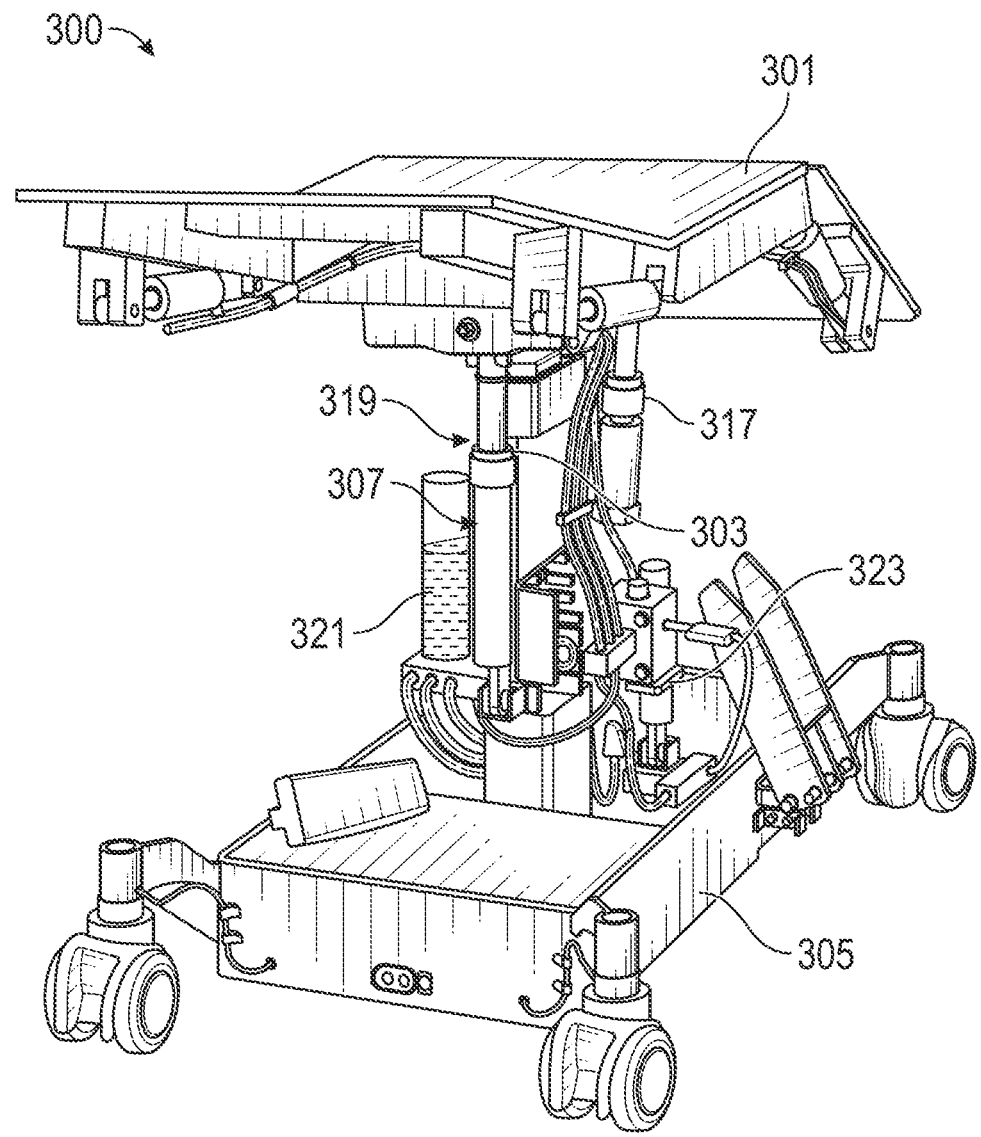
FIG. 23 illustrates an embodiment of a platform including a tilt mechanism according to one embodiment.

FIG. 23 illustrates an embodiment of a robotic system 300 including a hydraulic tilt mechanism 307 for tilting a patient platform 301 thereof. In this example, the patient platform 301 is supported above a base 305 by a column 303. The hydraulic tilt mechanism 307 comprises a lateral tilt hydraulic piston 317 configured to be actuable to laterally tilt the patient platform 301 and a longitudinal tilt hydraulic piston 319 configured to be actuable to longitudinally tilt the patient platform 301. Further, because the hydraulic tilt mechanism 307 uses hydraulic pistons 317, 319 the system 300 also comprises a fluid reservoir 321, holding hydraulic fluid, and a pump 323 for actuating the hydraulic pistons 317, 319. As shown, the system 300 is configured to fit beneath the patient platform 301. However, the hydraulic tilt mechanism 307 (including the hydraulic pistons 317, 319, the fluid reservoir 321, and the pump 323) occupies significant space below the patient platform 301. In particular, the hydraulic tilt mechanism 307 occupies significant "swept" volume below the patient platform 301. As used here, "swept" volume is the space that is occupied by a particular mechanism (e.g., the hydraulic pistons) during tilt. Such a hydraulic tilt mechanism 307 can make it difficult, if not impossible, to fit the robotic arms and adjustable arm supports below the patient platform in the stowed configuration (see FIG. 21A). Thus, a tilt mechanism with a smaller form factor may be desirable.

Figure 28B:
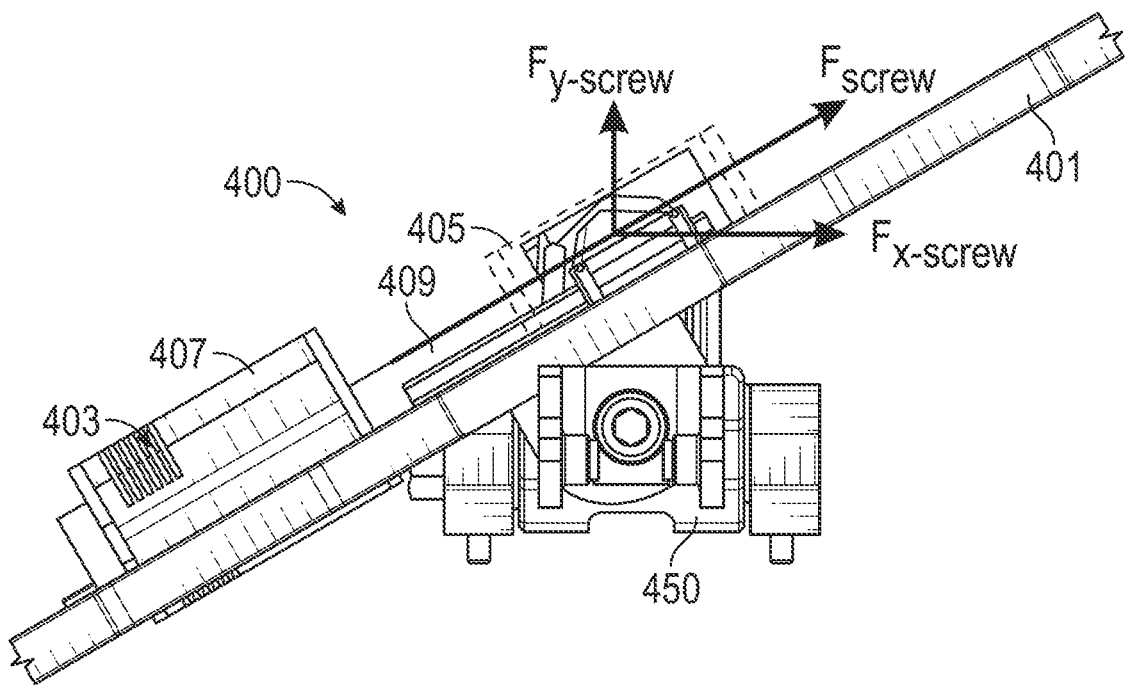
FIG. 28B is an end view of the lateral tilt mechanism of FIG. 25 illustrating components of the linear force shown in FIG. 28A.
Figure 29:
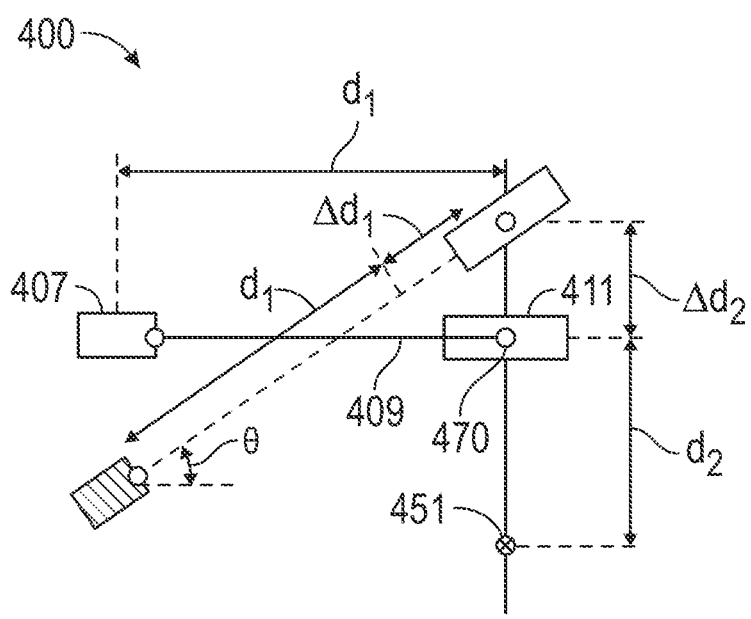
FIG. 29 schematically illustrates motion of a lateral tilt mechanism according to one embodiment.
Figure 30A:
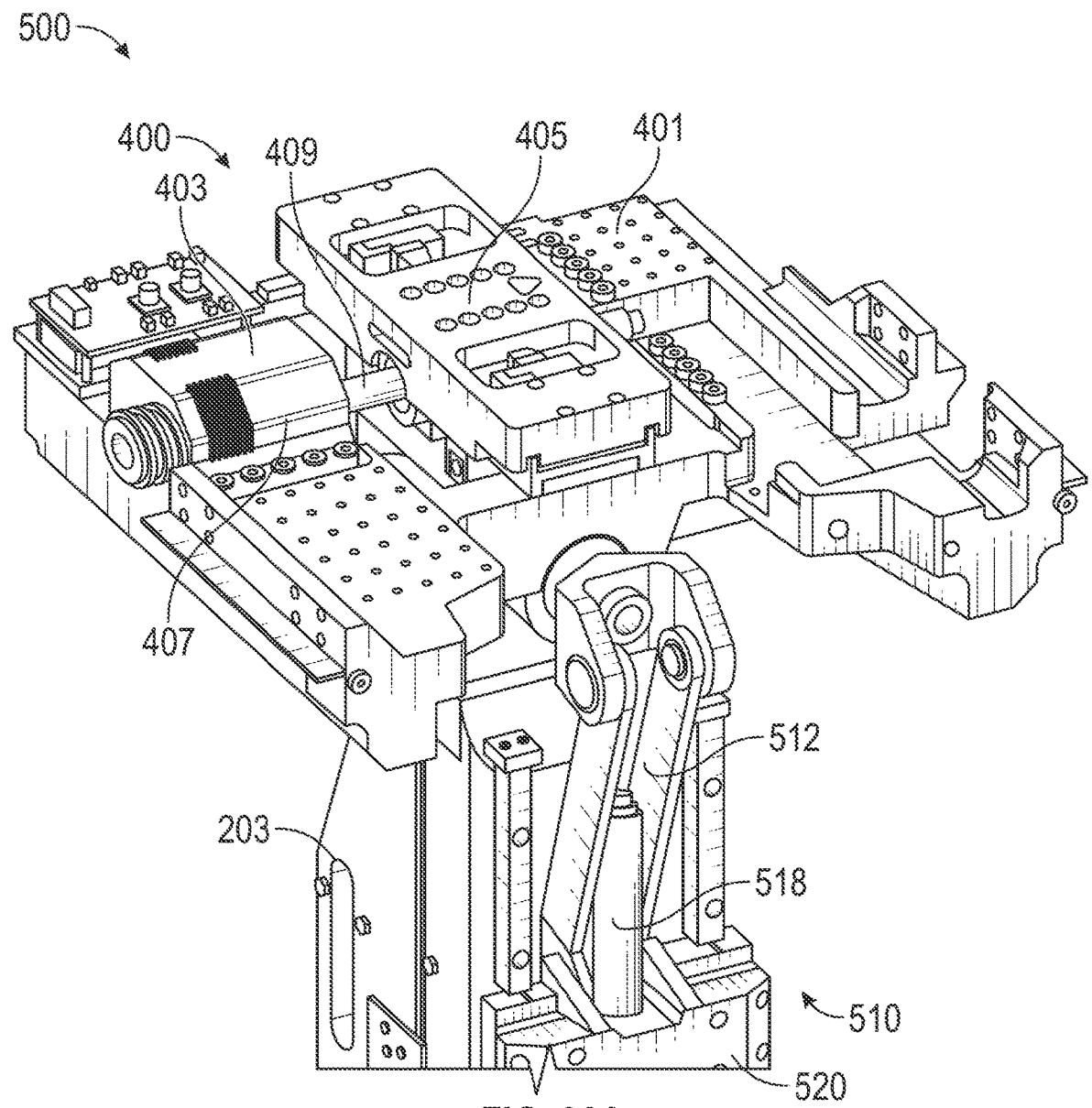
FIG. 30A is an isometric view of an embodiment of tilt mechanism for a patient platform of a robotic medical system that includes a lateral tilt mechanism and a longitudinal tilt mechanism.
Figure 30B:
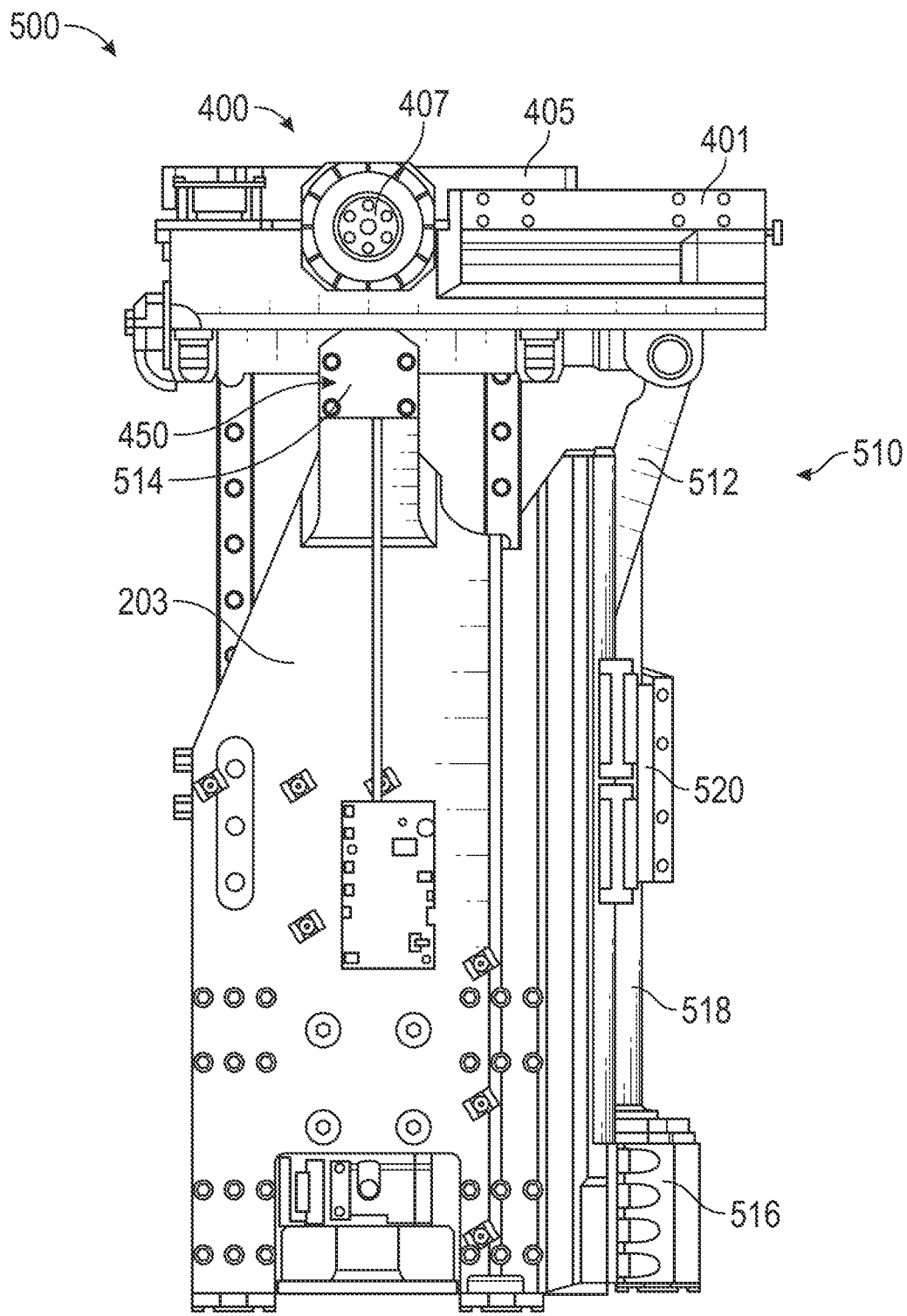
FIG. 30B illustrates a side view of the tilt mechanism of FIG. 30A.
Figure 31:
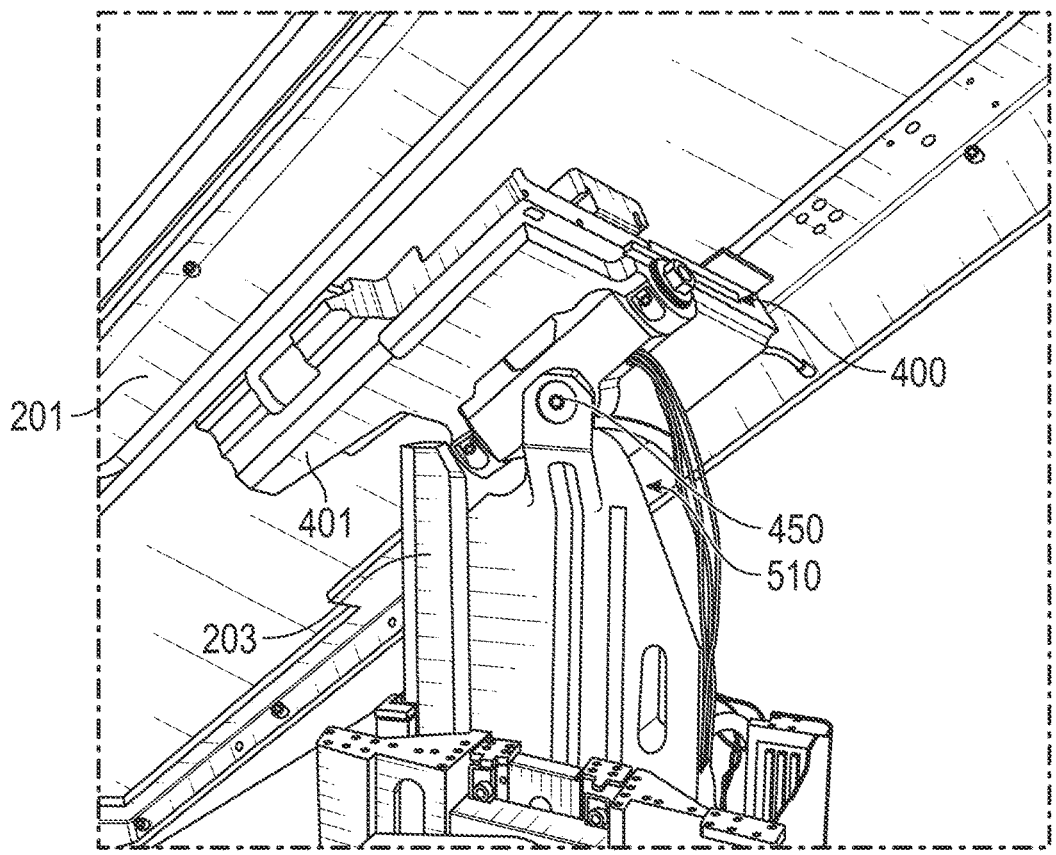
FIG. 31 is an isometric view of an embodiment of a patient platform of a robotic medical system that includes a tilt mechanism configured for simultaneous lateral and longitudinal tilt.

FIGS. 24A-29 relate to an embodiment of a lateral tilt mechanism 400 that can, in some embodiments, be used with a longitudinal tilt mechanism 510 as shown in FIGS. 30A-31. In some instances, a patient platform using the lateral tilt mechanism 400 can provide a number of improvements over the hydraulic tilt mechanism 307 of FIG. 23, as the lateral tilt mechanism 400 is configured to have a much lower-profile and small form factor. This allows it to be suitable for use with robotic medical systems that use the space below the patient platform for stowage of the robotic arms (see FIG. 21A). Additionally, although the following describes the lateral tilt mechanism 400 as configured for lateral tilt. A similar mechanism could be configured for longitudinal tilt.

Figure 24A:
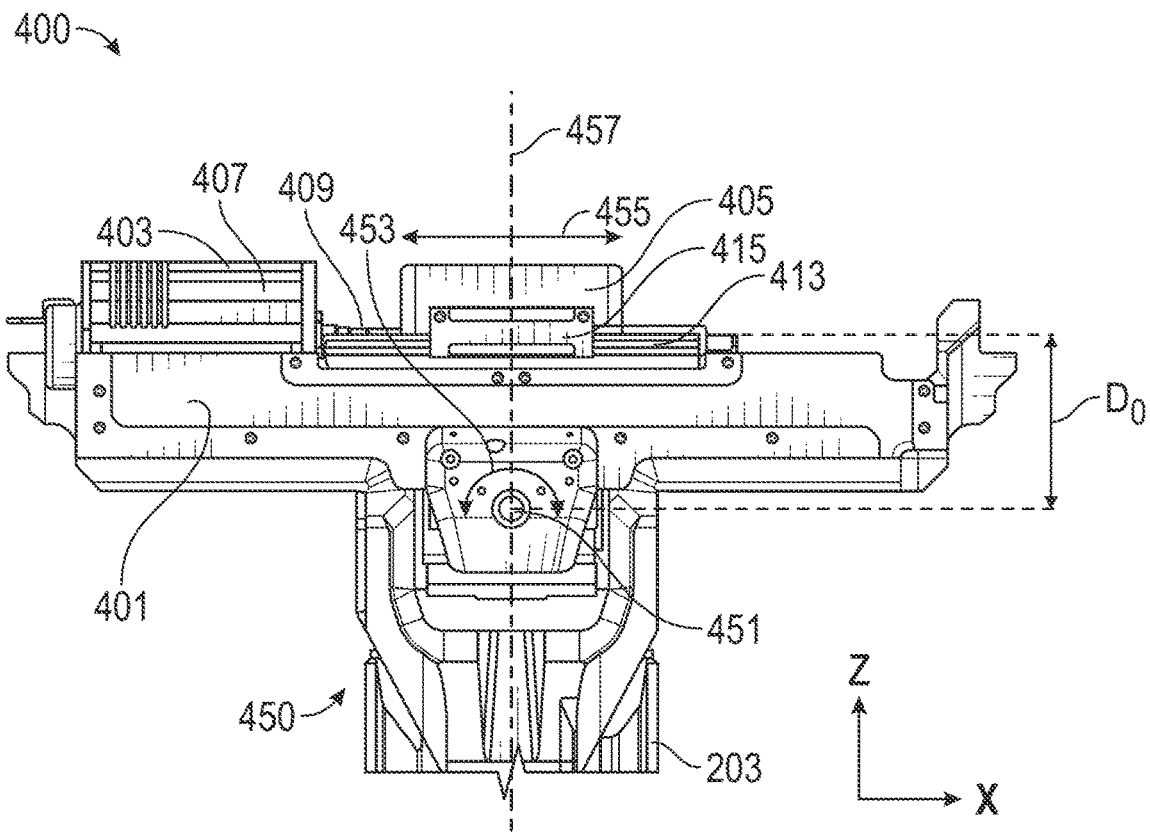
FIG. 24A illustrates an end view of an embodiment a lateral tilt mechanism for a patient platform of a robotic medical system in an untilted state.
Figure 24B:
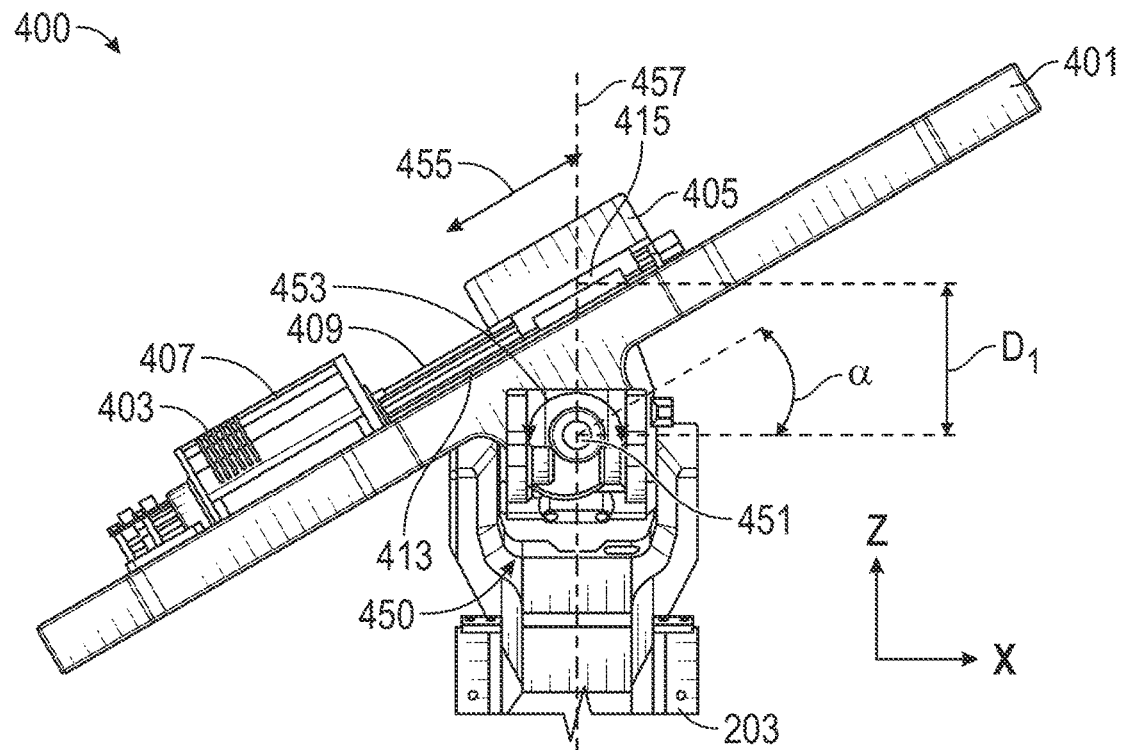
FIG. 24B is an end view of the lateral tilt mechanism of FIG. 24A in a first tilted configuration.
Figure 24C:
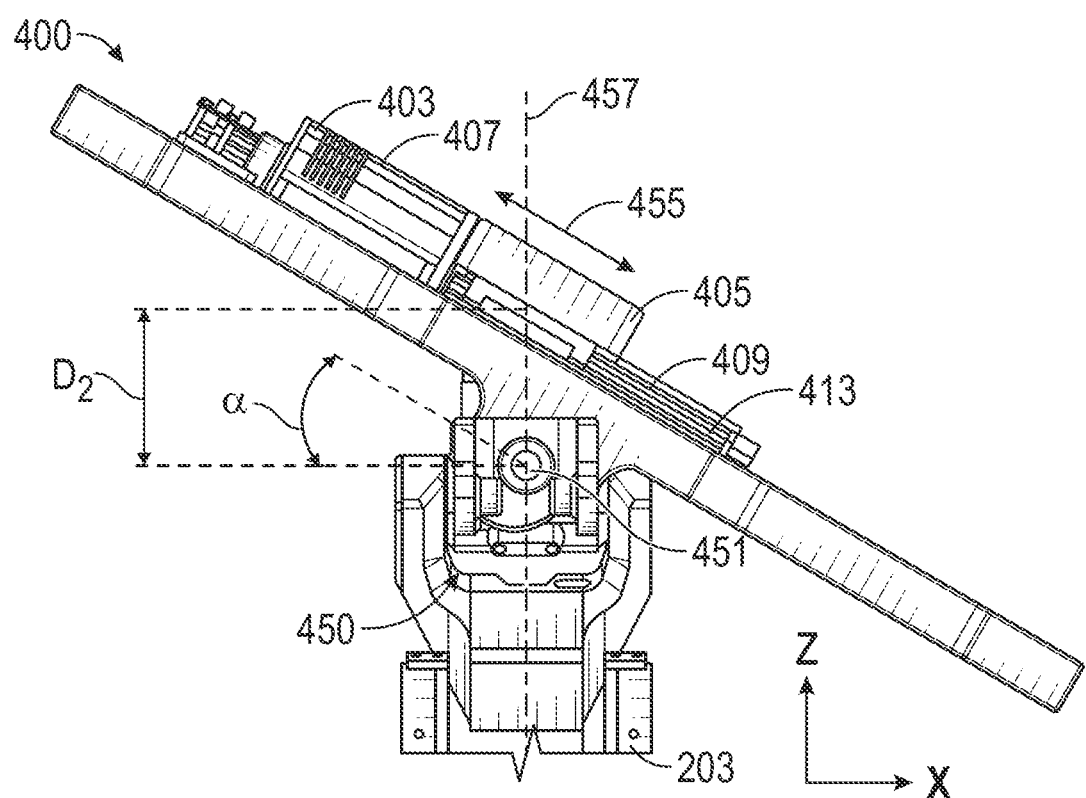
FIG. 24C is an end view of the lateral tilt mechanism of FIG. 24A in a second tilted configuration.

FIG. 24A illustrates an end view of the lateral tilt mechanism 400 in an untilted stated. As shown, the untilted state may be a horizontal state. The untilted state may be a default position of the lateral tilt mechanism 400. FIGS. 24B and 24C are end views illustrating the lateral tilt mechanism 400 in first and second tilted states. With reference first to FIG. 24A, the lateral tilt mechanism 400 comprises a pivot or tilt plate 401. The tilt plate 401 may comprise a generally flat or planar plate (see, for example, FIG. 30A). The tilt plate 401 may comprise various features, such as recesses, cut outs, or protrusions that provide room for or support one or more additional components of the lateral tilt mechanism 400. Thus, although the tilt plate 401 is described as generally flat or planar, this can refer to the shape generally, with the understanding that additional features may be formed on the tilt plate 401. For example, in some embodiments, the tilt plate 401 need not be completely flat. In some embodiments, the tilt plate 401 comprises a plate that extends generally within a plane.

As shown in FIG. 24A, the tilt plate 401 can be connected to a gimbal 450. The gimbal 450 can be part of or coupled to the column 203. Thus, in some embodiments, the gimbal 450 is positioned between the column 203 and the tilt plate 401. The gimbal 450 can be configured to allow the tilt plate 401 to pivot, rotate, or tilt relative to the column 203. In some embodiments, the gimbal 450 is configured to allow the tilt plate 401 to tilt in more than one direction. For example, in some embodiments, the gimbal 450 is configured to allow the tilt plate 401 to tilt in both lateral and longitudinal directions. In some embodiments, the gimbal 450 is configured to allow the tilt plate 401 to tilt in both lateral and longitudinal directions simultaneously (see, for example, FIG. 31).

In the embodiment illustrated in FIG. 24A, the gimbal 450 is configured to permit the tilt plate 401 to tilt laterally about a lateral tilt axis 451. The lateral tilt axis 451 may extend in a direction that is parallel to the y-axis (i.e., into the page). The tilt plate 401 can tilt about the lateral tilt axis 451 in the lateral tilt directions 453 illustrated with arrows. As noted previously, FIGS. 24B and 24C show the tilt plate 401 laterally tilted in two different positions. The gimbal 450 of the embodiment illustrated in FIG. 24A can also be configured to provide longitudinal tilt as will be described below with reference to FIGS. 30A-31.

The tilt plate 401 may be configured to attach to an underside of the patient platform 201 (not illustrated in FIG. 24A, but see, for example, FIGS. 20A-21B and FIG. 31). Thus, in some embodiments, the gimbal 450 and tilt plate 401 are positioned between the column 203 and the patient platform 201 so as to allow the patient platform 201 to tilt relative to the column 203.

With continued reference to FIG. 24A, the lateral tilt mechanism 400 can further include a linear actuator 403 mounted on the tilt plate 401. The linear actuator 403 can be configured to apply a force to a pivot housing 405. The linear actuator 403 can be fixedly mounted to the tilt plate 401. As the linear actuator 403 applies the force to the pivot housing 405, the pivot housing 405 can move back and forth along the tilt plate 401. For example, the pivot housing 405 can move back and forth in the directions 455 indicated with arrows in FIG. 24A. As will be described with more detail below, as the pivot housing 405 moves back and forth, the tilt plate 401 tilts laterally (see FIGS. 24B and 24C) about that lateral tilt axis 451.

In the illustrated embodiment, the linear actuator 403 comprises a screw drive assembly. The screw drive assembly can comprise a motor 407, a lead screw 409, and a screw nut housing 411 (within the pivot housing 405, but not visible in FIG. 24A; see FIGS. 25-27 which show the screw nut housing 411). The motor 407 can be fixedly mounted to the tilt plate 401. The motor 407 can be configured to rotate the lead screw 409. The lead screw 409 may extend along the x-axis in the untilted state. More generally, the lead screw 409 can extend along the plane of the tilt plate 401 (e.g., in the plate of the tilt plate 401 or parallel to it) and in a direction orthogonal to the lateral tilt axis 451. The screw nut housing 411 can be mounted on the lead screw 409. As the lead screw 409 rotates, the screw nut housing 411 can travel forward and backward along the lead screw 409. The screw nut housing 411 can be mounted within the pivot housing 405 (see FIG. 25). Thus, forces transmitted to the screw nut housing 411 can also be transmitted to the pivot housing 405, and, as the screw nut housing 411 moves back and forth along the lead screw 409, the pivot housing 405 can move back and forth with it (e.g., in the directions 455). An example screw drive assembly is shown in more detail in FIGS. 25 and 26, described below. Although the illustrated linear actuator 403 is a screw drive assembly, other types of linear actuators can also be used.

As illustrated in FIG. 24A, in some embodiments, the lateral tilt mechanism 400 can comprise one or more linear guides 413 that extend in a direction parallel to the lead screw 409. The linear guides 413 can comprise rails. The pivot housing 405 may comprise one or more carriages 415 that are mounted on the one or more linear guides 413. The one or more carriages 415 can be configured to translate along the one or more linear guides 413 as the pivot housing 405 moves backwards and forwards in the directions 455. In some embodiments, the one or more linear guides 413 provide stability for the lateral tilt mechanism 400. In some embodiments the one or more linear guides 413 can be omitted. The one or more linear guides 413 will be described in more detail with reference to FIGS. 25 and 26, which show the one or more linear guides 413 in greater detail.

The linear actuator 403 is configured to apply a linear force to the pivot housing 405 at a position located above the lateral tilt axis 451. For example, as illustrated in FIG. 24A, when the tilt plate 401 is in an untilted state, the linear actuator 403 applies the linear force to the pivot housing 405 at a distance $D_O$ above the lateral tilt axis 451. The distance $D_O$ can be measured along an axis 457 as shown. In the untilted state, the axis 457 is aligned with the vertical or z-axis. However, more generally, if the tilt plate 401 is longitudinally tilted, the axis 457 can extend perpendicularly to the angle of longitudinal tilt. Stated another way, the axis 457 can be perpendicular to the lateral tilt axis within the z-y plane. As will be shown with reference to the following figures, as the tilt plate 401 tilts laterally, the distance (measured along the axis 457) between the lateral tilt axis 451 and the application of the linear force to the pivot housing 405 varies (compare $D_O$ of FIG. 24A with D.sub.1 of FIG. 24B and D.sub.2 of FIG. 24C; see also FIG. 29 and the corresponding description). That is, as the linear actuator 403 applies the linear force to the pivot housing 405, the distance between the point at which the linear force is applied to the pivot housing 405 changes, which, as described below, causes the tilt plate 401 to tilt about the lateral tilt axis 451.

FIG. 24B is an end view of the lateral tilt mechanism of FIG. 24A in a first tilted state. In the illustrated state, the motor 407 of the linear actuator 403 has driven the pivot housing 405 in a direction away from the motor 407 along the direction 455. As shown, the direction 455 remains parallel to the plane of the pivot plate 401. This can be because the pivot housing 405 moves along the lead screw 409 and the linear rails 413, which are each fixed with respect the pivot plate 401. The screw nut housing 411 (within the pivot housing 405) has moved along the lead screw 409, causing the pivot housing 405 to translate along the liner guides 413. Such motion causes the tilt plate 401 to tilt as shown. In the illustrated embodiment, the tilt plate 401 is shown tilted in a first direction at a lateral tilt angle .alpha. In some embodiments, the range of the lateral tilt angle .alpha. can be as described above with reference to FIG. 21A.

Figure 26:
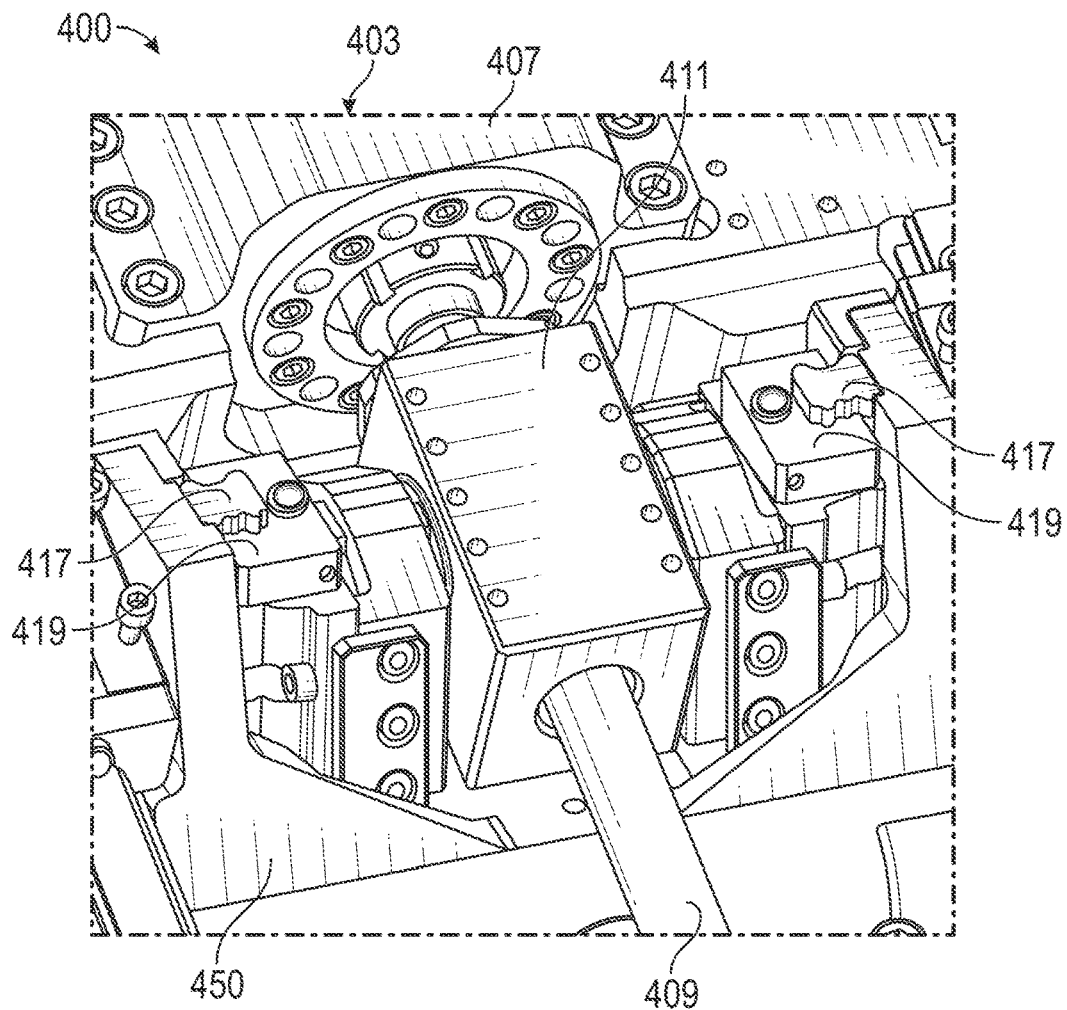
FIG. 26 is an isometric view of the lateral tilt mechanism of FIG. 25 illustrating a screw nut housing thereof.
Figure 27:
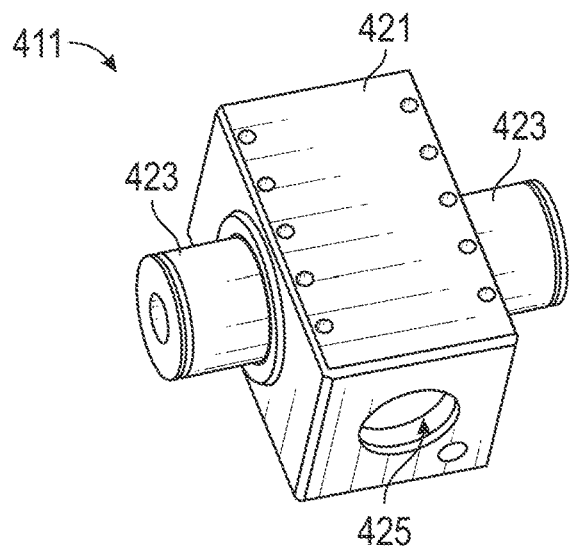
FIG. 27 is an isometric view of the screw nut housing of FIG. 26.

As shown in FIG. 24B, during tilting of the tilt plate 24B, the pivot housing 405 remains positioned above the lateral tilt axis 451 along the axis 457. As described below, this can be because the pivot housing is also slidingly mounted on an additional linear guide 417 (see FIGS. 25-27) that can be fixed with respect to the gimbal 450 so as to extend along the axis 457. A distance D.sub.1, measured along the axis 457 between the lateral tilt axis 451 and the application of the linear force to the pivot housing 405 is shown in FIG. 24B. Notably, the distance D.sub.1 (FIG. 24B) is larger than the distance $D_O$ (FIG. 24A). This is because, as will be described in more detail below, the pivot housing 405 translates upwardly along the axis 457 as the tilt plate 401 tilts. This upward translation of the pivot housing 405 is a unique feature of the tilt mechanism 400. As the linear actuator 403 applies a linear force to the pivot housing 405 along the plane of the tilt plate, the distance between the linear actuator 403 (e.g., the motor 407) and the pivot housing 405 increases along the direction 455. As mentioned previously, the linear actuator 403 can be fixed to the tilt plate 401, while the pivot housing 405 is not. The pivot housing 405 may be free to move along the plane of the tilt plate 401 in the direction 455. Further, the pivot housing 405 can be constrained such that it is always positioned on the axis 457. For example, the tilt mechanism 400 can include the linear guide 417 as shown in FIGS. 25-27 (described below) that constrains the pivot housing 405 such that it moves along the axis 457.

FIG. 24C is an end view of the lateral tilt mechanism of FIG. 24A in a second tilted state. In the illustrated state, the motor 407 of the linear actuator 403 has driven the pivot housing 405 in a direction toward the motor 407 along the direction 455. The screw nut housing 411 (within the pivot housing 405) has moved along the lead screw 409, causing the pivot housing 405 to translate along the liner guides 413 towards the motor 407. Such motion causes the tilt plate 401 to tilt as shown. In the illustrated embodiment, the tilt plate 401 is shown tilted in a second direction at a lateral tilt angle .alpha. Again, the lateral tilt angle .alpha. can have the range previously described.

Similar to the position shown in FIG. 24B, in the position of FIG. 24C, the pivot housing 401 remains positioned above the lateral tilt axis 451 along the axis 457. As mentioned above, this can be because the pivot housing 405 is further constrained by linear guides 417 such that it can translate along the axis 457. A distance D.sub.2, measured along the axis 457 between the lateral tilt axis 451 and the application of the linear force to the pivot housing 405 is shown in FIG. 24C. Notably, the distance D.sub.2 (FIG. 24B) is larger than the distance $D_O$ (FIG. 24A). This is because, the pivot housing 405 translates upwardly along the axis 457 as the tilt plate 401 tilts. In some embodiments, if the angle .alpha. of FIG. 24C is equal to the angle .alpha. of FIG. 24B, the distance D.sub.2 (FIG. 24C) can be equal to the distance D.sub.1 (FIG. 24B).

Figure 25:
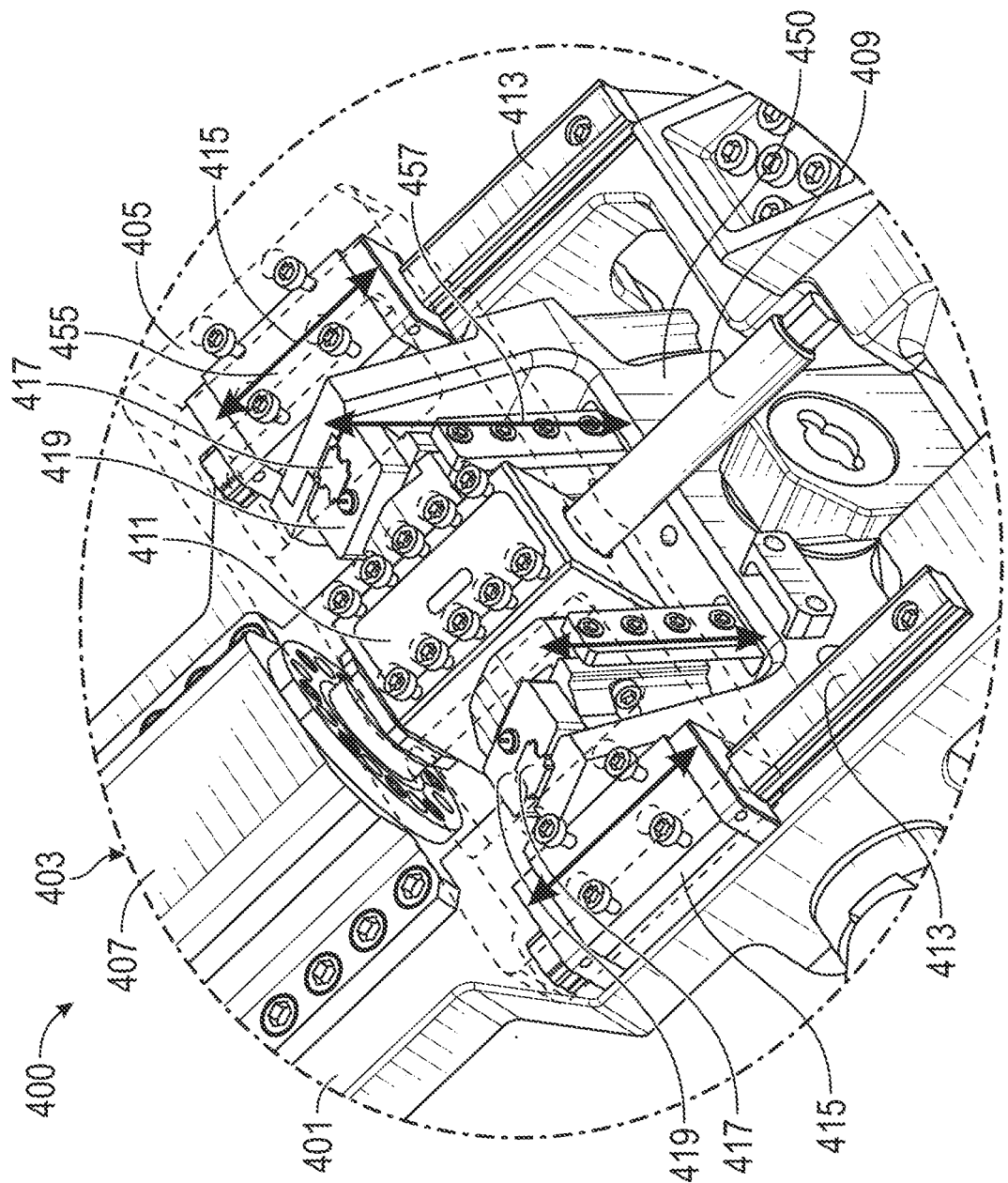
FIG. 25 is an isometric view of an embodiment a lateral tilt mechanism for a patient platform of a robotic medical system illustrating a linear actuator, pivot housing, and linear guides thereof.

FIG. 25 is an isometric view of an embodiment the lateral tilt mechanism 400. FIG. 25 illustrates the linear actuator 403, pivot housing 405, and linear guides 413, 417 thereof according to one embodiment. In FIG. 25, the pivot housing 405 is illustrated as transparent such that the internal features of the pivot housing 405 and the components below the pivot housing 405 can be seen. FIG. 25 illustrates the tilt mechanism 400 in a tilted state similar to the state shown in FIG. 24C.

As illustrated in FIG. 25, the linear actuator 403 can comprise the motor 407, the lead screw 409, and the screw nut housing 411. As shown, the screw nut housing 411 is mounted on the lead screw 409 (see also FIG. 26). As the motor 407 rotates the lead screw 409, the screw nut housing 411 moves back and forth along the lead screw 409 in the directions 455. The screw nut housing 411 can be positioned within the pivot housing 405. Further, the screw nut housing 411 can be connected to the pivot housing 405. In the illustrated embodiment, the screw nut housing 411 is bolted to the pivot housing 405, although other connection methods are possible. Because the screw nut housing 411 is connected to the pivot housing 405, as the screw nut housing 411 moves along the lead screw 409, the pivot housing 405 moves along the lead screw 409 with it. In this manner, the linear actuator 403 can be configured to cause the pivot housing 409 to move back and forth in the directions 455.

As shown in FIG. 25, the pivot housing 405 can include carriages 415 that can be slidingly engaged with linear guides 413. The linear guides 413 can extend along the tilt plate 401 in the directions 455. The linear guides 413 can be attached to or otherwise fixed with respect to the tilt plate 401. In the illustrated embodiment, the tilt mechanism 400 includes a pair of linear guides 413 positioned on opposite sides of the screw nut housing 411. In some embodiments, other numbers of linear guides 413 can be used. For example, one, two, three, four or more linear guides 413 can be used. In some embodiments, the linear guides 413 provide stability as the pivot housing 405 translates back and forth along the linear guides 413 in the directions 455. In some embodiments, the linear guides 413 can be omitted. For example, even without the linear guides 413, the pivot housing 405 would translate back and forth in the directions 455 along the lead screw 409. The linear guides 413 can be configured as rails.

FIG. 25 further illustrates the linear guides 417. As mentioned above, the linear guides 417 can further constrain the motion of the pivot housing 405 such that it translates up and down along the axis 457. The linear guides 417 can be attached or otherwise fixed with respect to a piece of the gimbal 450. Carriages 419, which are connected to the pivot housing 405, can be configured to translate along the linear guides 417. Because the tilt plate 401 tilts with respect to the gimbal 450 and the linear guides 417 are attached to the gimbal 450, the tilt plate 401 also tilts with respect to the linear guides 417. That is regardless of the lateral tilt angle of the tilt plate 401, the linear guides 417 extend along the axis 457. This constrains the motion of the pivot housing 405 such that it can move along the axis 457. This also maintains that the pivot housing 405 is located above (measured along the axis 457) the lateral pivot axis (see FIGS. 24A, 24B, and 24C). The linear guides 417 can be configured as rails.

In the illustrated embodiment, the tilt mechanism 400 includes a pair of linear guides 417, with one lateral guide 417 positioned on each side of the screw nut housing 411. In some embodiments, other numbers of linear guides 417 can be used. For example, one, two, three, four or more linear guides 417 can be used. Further, in the illustrated embodiment, the pair of linear guides 417 are positioned within the pair of linear guides 413. This need not be the case in all embodiments. For example, the pair of linear guides 413 could be positioned inside the pair of linear guides 417. As mentioned previously, the linear guides 413 can provide added stability for the tilt mechanism 400 can be omitted in some embodiments.

FIG. 26 is an isometric view of the lateral tilt mechanism 400 illustrating a more detailed view of the linear guides 417 and the screw nut housing 411. In FIG. 26, the pivot housing 405 is removed to better illustrate the linear guides 417 and the screw nut housing 411. As shown, the screw nut housing 411 is positioned on the lead screw 409. The screw nut housing 411 is also slidingly engaged with the linear guides 417 via carriages 419. The screw nut housing 411 can be connected to the carriages 419 in a manner that permits the screw nut housing 411 to rotate relative to the carriages 419 and the linear guides 417.

FIG. 27 is an isometric view of the screw nut housing 411. As shown, the screw nut housing 411 can comprise a base component or body 421. In the illustrated embodiment, the body 421 is rectangular, but other shapes for the body 421 are possible. An opening 425 can extend through the body 421. The opening 425 can be configured to receive the lead screw 409. In some embodiments, an inner surface of the opening 425 is threaded to engage corresponding threads on the lead screw 409. As shown, posts 423 can extend laterally from the body 421. The posts 423 can be configured to be received within corresponding recesses formed on the carriages 419. The posts 423 can rotate within the corresponding recesses to allow the screw nut housing 411 to rotate with respect to the carriages 419.

FIGS. 28A and 28B illustrates the transfer of forces from the linear actuator 403 to the pivot housing 405 and screw nut housing 411. FIG. 28A is an isometric view of the lateral tilt mechanism 400 illustrating application of a linear force, and FIG. 28B is an end view of the lateral tilt mechanism 400 illustrating components of the linear force.

As illustrated in FIG. 28A, the linear actuator 403 is configured to apply a linear force F.sub.screw to the screw nut housing 411 (and correspondingly to the pivot housing 405). The force F.sub.screw acts in a direction parallel to the lead screw 409. Because the motor 407 and lead screw 409 are fixedly mounted with respect to the tilt plate 401, the relative orientation of F.sub.screw and the tilt plate 401 is not dependent on the lateral tilt angle of the tilt plate 401. Rather, the direction of F.sub.screw is in a direction parallel to the plane of the tilt plate 401.

As shown in FIG. 28B, the force F.sub.screw can be broken into component vectors F.sub.x and F.sub.y. Each of the linear guides 413, 417 is configured to react to one of the two component forces F.sub.x and F.sub.y. For example, the linear guides 417 can be configured to react to F.sub.x to cause vertical translation or translation along the axis 457 (see FIGS. 24A, 24B, and 24C) of the pivot housing 405. As described previously, translation along the axis 457 causes the tilt plate 401 to tilt about the latera tilt axis. More particularly, in the illustrated embodiment, as the motor 407 drives the lead screw 409 to cause linear motion of the screw nut housing 411 and tilt housing 405, the force F.sub.x is countered by the linear guides 417, thereby driving the carriages 419 up along the fixed rails. This causes lateral tilt.

The linear guides 413 can be configured to react to the force F.sub.y to cause translation of the pivot housing 405 along the directions 455 (see FIGS. 24A, 24B, and 24C). As mentioned previously, the linear guides 413 may advantageously provide stability. For example, the linear guides 413 can protect the lead screw 409 from bending or breaking beyond a maximum deviation.

FIG. 29 schematically illustrates example motion of a lateral tilt mechanism 400 according to one embodiment. The motor 407, lead screw 409, and screw nut housing 411 are each illustrated schematically. The lateral tilt mechanism 400 is shown in solid lines in an untilted state and in dashed lines in a tilted state. As shown, as the motor 407 is actuated, the distance between the motor 407 and the screw nut housing 411 changes by .DELTA.d.sub.1. This causes the screw nut housing 411 to be driven upwards along a vertical trajectory created by the linear guides 413, which causes the tilt plate 401 to tilt. As the screw nut housing 411 translates upwards, the pivot point 470 of the screw nut housing 411 also translates vertically. Thus, from the untilted state the tilted state, the position of the pivot point 470 of the screw nut housing has moved up by Adz with respect to the lateral tilt axis 451.

As mentioned before, the lateral tilt mechanism 400 may comprise a low profile or small profile. This may be because the lateral tilt mechanism 400 can mount on a substantially flat or planar tilt plate 401, and the linear actuator 403 acts in a direction that is parallel to the plane of the tilt plate 401. Due to the low profile of the lateral tilt mechanism 400, in some embodiments, the lateral tilt mechanism 400 can be coupled to a longitudinal (or Trendelenburg) tilt mechanism. In some embodiments, the lateral tilt mechanism 400 can be stacked on top of the longitudinal tilt mechanism. In this manner, a tilt mechanism can be configured to allow for both lateral and longitudinal (or Trendelenburg) tilt.

FIGS. 30A and 30B illustrate an embodiment of tilt mechanism 500 for the patient platform 201 of a robotic medical system 200 that includes the lateral tilt mechanism 400 and a longitudinal tilt mechanism 510. FIG. 30A is an isometric view and FIG. 30B is a side view. In the illustrated embodiment of the tilt mechanism 500, the lateral tilt mechanism 400 is stacked on top of the longitudinal tilt mechanism 510.

In the illustrated embodiment, the lateral tilt mechanism 400 is configured as described above, including, for example, the tilt plate 401, linear actuator 403, and pivot housing 405. To enable longitudinal tilt, the longitudinal tilt mechanism 510 can also be included. In the illustrated embodiment, the longitudinal tilt mechanism 510 comprises a longitudinal link 512. The longitudinal link 512 can be attached to the lateral tilt plate 410 (see FIG. 30A). The longitudinal link 512 can also attached to the column 203. For example, in the illustrated embodiment, the longitudinal link 512 is attached to the column 203 with a carriage 520 that is mounted on a lead screw 518. A motor 516 can be mounted to the column 203 and configured to rotate the lead screw 518. As the lead screw rotates, the carriage 520 is driven up and down along the column 203. As the carriage 520 is driven up and down along the column 203, the longitudinal link 512 acts on the tilt plate 401 to cause the tilt plate 401 to tilt longitudinally. As shown in FIG. 30B, the longitudinal tilt mechanism 510 can be configured to cause the tilt plate 401 to tilt about a longitudinal tilt axis 451.

FIG. 31 illustrates that the tilt mechanism 500 can be configured for both simultaneous lateral and longitudinal tilt using the lateral tilt mechanism 400 and the longitudinal tilt mechanism 510, respectively. As noted previously, in some embodiments, the tilt mechanism 500 is configured to allow at least a lateral tilt angle of about 15 degrees, 20 degrees, 25 degrees, 30 degrees, 35 degrees, 40 degrees, 45 degrees or more relative to the untilted state while simultaneously allowing at least a longitudinal tilt angle of about 15 degrees, 20 degrees, 25 degrees, 30 degrees, 35 degrees, 40 degrees, 45 degrees, 50 degrees, 55 degrees, 60 degrees or more relative to the untilted state. As a specific example, the tilt mechanism 500 can be configured to all the patient platform 201 to have lateral tilt of 30 degrees and concurrent longitudinal tilt of 45 degrees as illustrated in FIG. 31.

Figure 32:
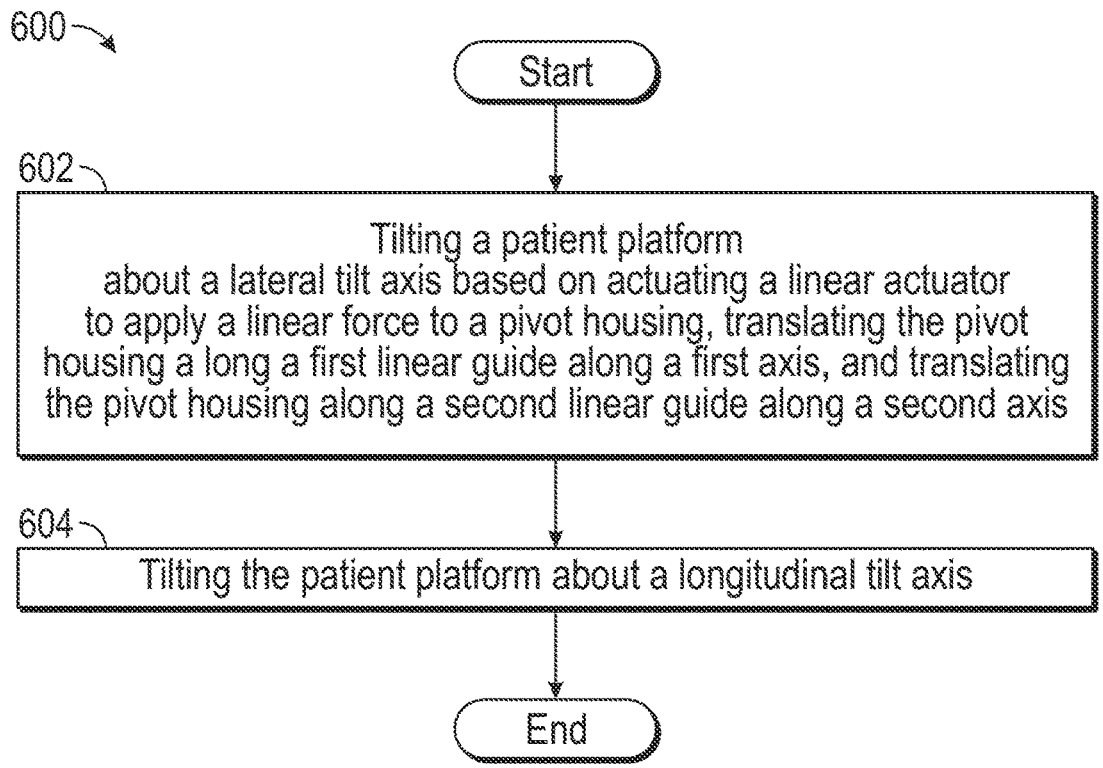
FIG. 32 is a flowchart illustrating an embodiment of a method for controlling tilt of a patient platform of a robotic medical system.

FIG. 32 is a flowchart illustrating an embodiment of a method 600 for controlling tilt of a patient platform of a robotic medical system. The method 600 may begin at block 602 at which the patient platform is tilted above a lateral tilt axis based on actuating a linear actuator to apply a linear force to a pivot housing, translating the pivot housing along a first linear guide along a first axis, and translating the pivot housing along a second linear guide along a second axis.

In some embodiments, the first linear guide can comprise the linear guide 413 discussed above, and the second linear guide can comprise the linear guide 417 discussed above. In some embodiments, first linear guide 413 comprises the lead screw 409. In some embodiments, the first axis is parallel to the linear force and the second axis is not parallel to the first axis.

In some embodiments, actuating the linear actuator comprises driving a lead screw with a motor. In some embodiments, the pivot housing comprises a screw nut housing mounted on the lead screw. In some embodiments, the motor is attached to a tilt plate that supports the patient platform, and wherein the first linear guide is attached to the tilt plate. In some embodiments, the second linear guide is attached to a gimbal, such as the gimbal 450.

As illustrated in FIG. 32, at block 604, the method 600 comprises pivoting the gimbal relative to a column that supports the patient platform to tilt the patient platform about a longitudinal tilt axis. In some embodiments, pivoting the gimbal relative to a column comprises driving a longitudinal link, such as the longitudinal link 512, with a longitudinal linear actuator that translates along an axis of the column, such as the motor 516, lead screw 518, and carriage 520.

In some embodiments, blocks 602 and 604 can be performed concurrently such that the method 600 comprises tilting the patient platform about the lateral tilt axis and the longitudinal tilt axis simultaneously.

In some embodiments, the method 600 further comprises performing a robotic medical procedure on a patient supported on the patient platform.

Figure 33A:
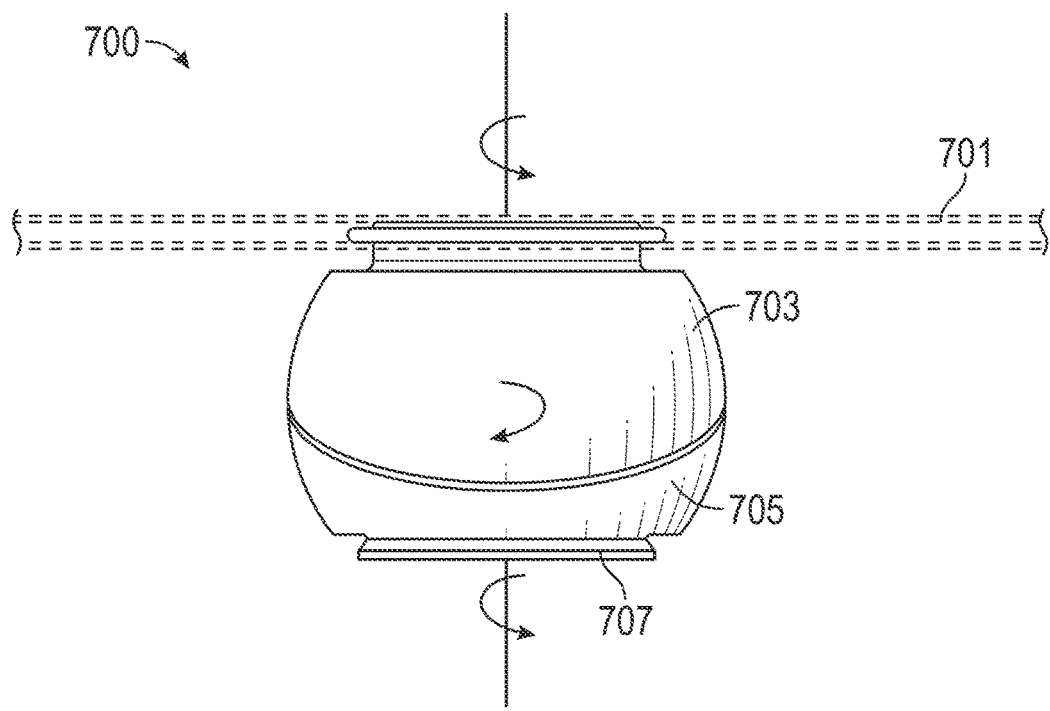
FIG. 33A illustrates a side view of an embodiment to an orthodrome tilt mechanism for a patient platform of a robotic medical system
Figure 33B:
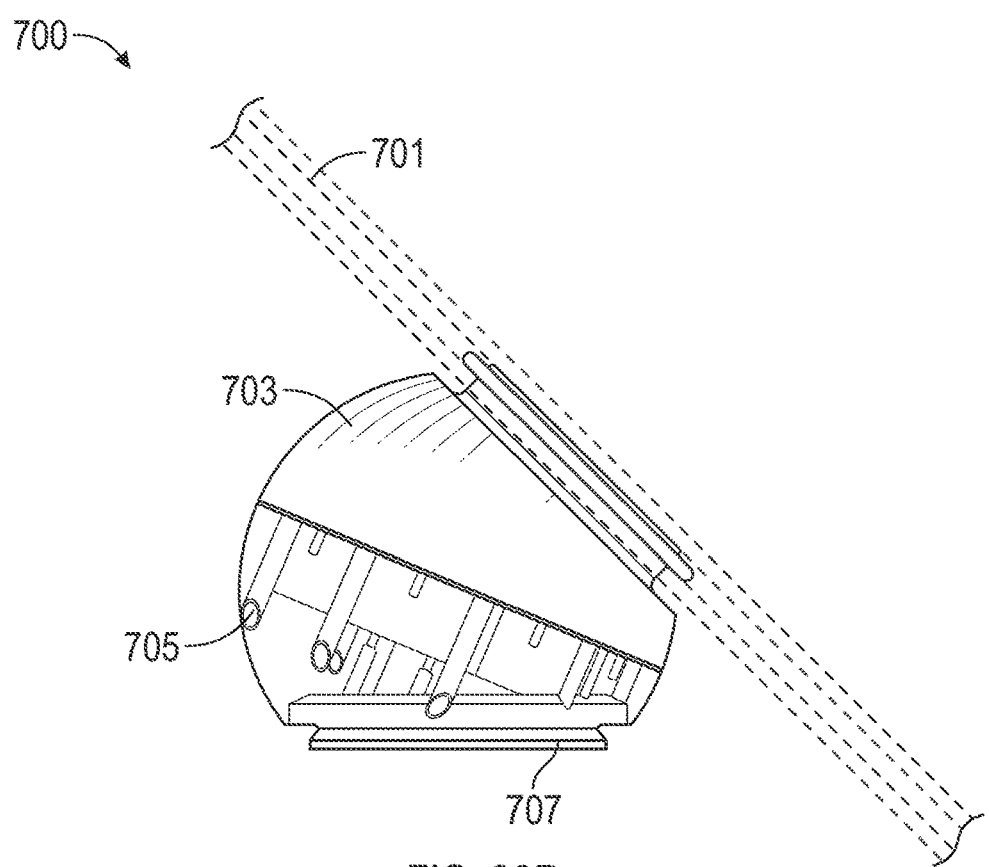
FIG. 33B illustrates the orthodrome tilt mechanism of FIG. 33A in a tilted configuration.
Figure 33C:
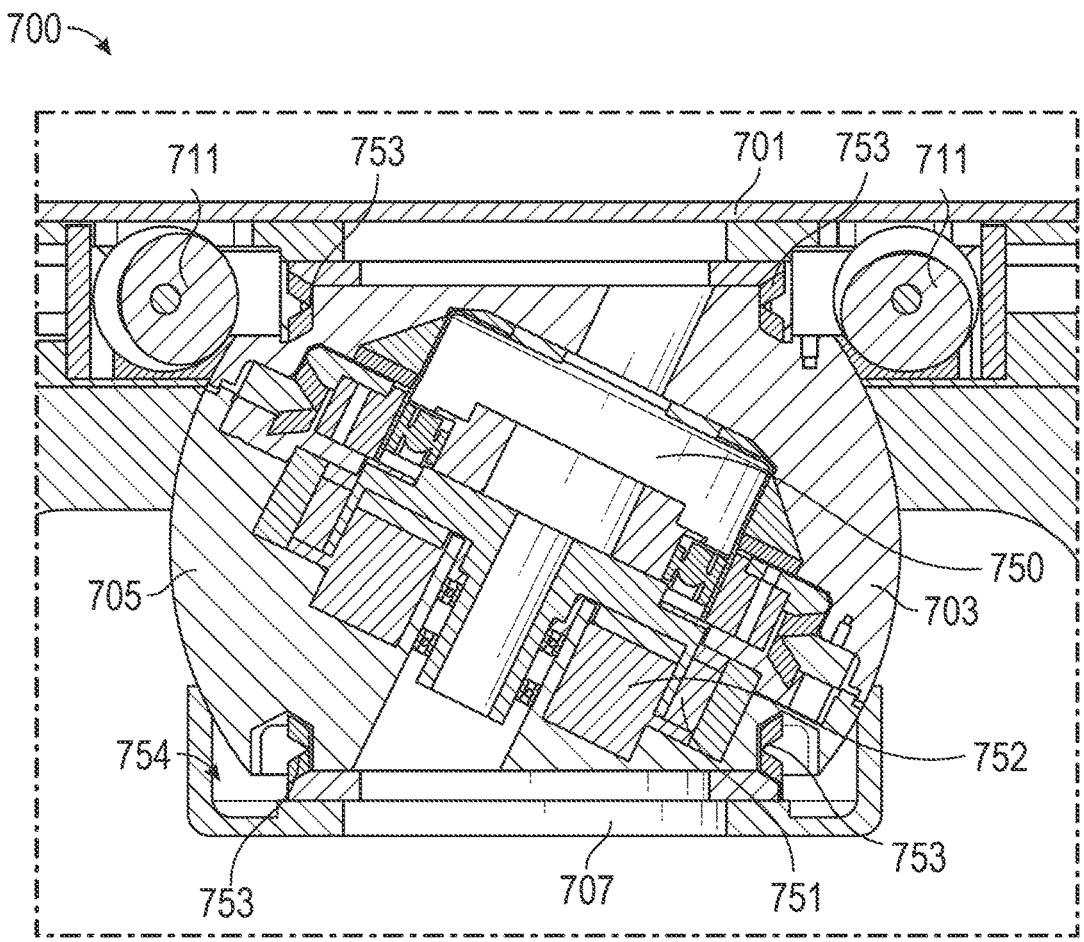
FIG. 33C illustrates a cross-sectional view of the orthodrome tilt mechanism of FIG. 33A.

FIGS. 33A-33E illustrate another embodiment of a tilt mechanism 700 that is configured to provide lateral and longitudinal tilt. In the illustrated embodiment, the tilt mechanism 700 comprises an orthodrome tilt mechanism for tilting a patient platform 701 of a robotic medical system. FIG. 33A illustrates a side view of the tilt mechanism 700 in an untilted position, and FIG. 33B illustrates the tilt mechanism 700 in a tilted position. FIG. 33C is a cross-sectional view of the tilt mechanism 700.

With reference to FIGS. 33A-33C, the tilt mechanism 700 comprises an orthodrome swivel that enables three rotating degrees of freedom, including Trendelenburg (e.g., longitudinal tilt), lateral tilt, and a combination of positions or angles in between. In particular, the tilt mechanism 700 comprises a first rotating portion 703 and a second rotating portion 705. The first and second rotating portions 703, 705 together comprise a generally spherical shape. However, as illustrated in FIG. 33A, the first and second rotating portions 703, 705 are joined at a non-orthogonal angle with respect to an axis of the column to which they are attached. The first rotating portion 703 can rotate relative to the second rotating portion 705. Further, the patient platform 701 can rotate relative to the first rotating portion 703. The second rotating portion 705 can be coupled to a column 707 (only a portion of the column 707 is illustrated in FIGS. 33A-33C. By rotating each of the patient platform 701, the first rotating portion 703, and the second rotating portion 705 to difference positions, lateral and longitudinal tilt of the patient platform 701 can be achieved. In one example, the tilt mechanism 700, the three rotating degrees of freedom are used to position the patient in up to 52 degrees of longitudinal tilt, up to 52 degrees of tilt, and a combination of angles in between.

As shown in FIG. 33C, the tilt mechanism 700 may comprise a motor 751 and a gearbox 750. The motor 751 and gearbox 750 can be configured to drive rotation of the first rotating portion 703 relative to the second rotating portion 705. The tilt mechanism 700 may also include brake 752, as shown. The brake 752 can be configured to be secure the patient platform 701 in position after the tilt mechanism 700 has been rotated to the desired position so as to maintain the patient platform 701 in a stable position. In some embodiments, an additional motor and gearbox (or other driving mechanism) can be included to drive rotation of the second rotating portion 705 relative to the column 707. For example, a motor and gearbox can be included in the space 754 to drive rotation of the second rotating portion 705 relative to the column 707. In other embodiments, the driving mechanism for rotating of the second rotating portion 705 relative to the column 707 can be positioned in other places, such as within the column 707 or within the second rotating portion 705. As described with more detail with reference to FIGS. 33D and 33E, the tilt mechanism 700 can include one or more worm drives 711 configured to drive rotation of the patient platform 701 relative to the first rotating portion 703. In some embodiments, other driving mechanisms (e.g., motors) can be used to rotate the patient platform 701 relative to the first rotating portion 705. Bearings 753 can be included to facilitate relative rotation of the various components of the tilt mechanism 700.

Figure 33D:
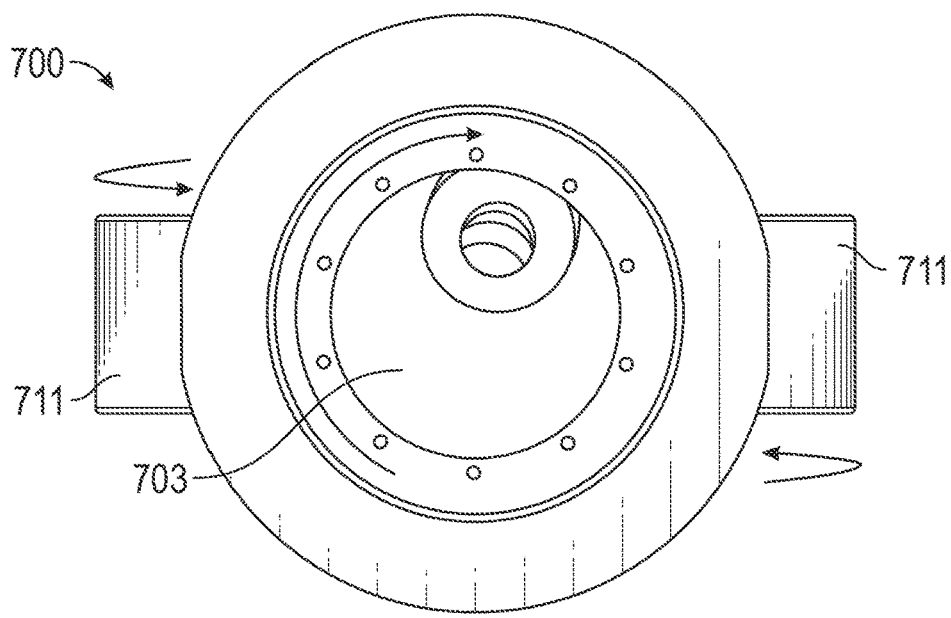
FIG. 33D is a top view of the orthodrome tilt mechanism of FIG. 33A.
Figure 33E:
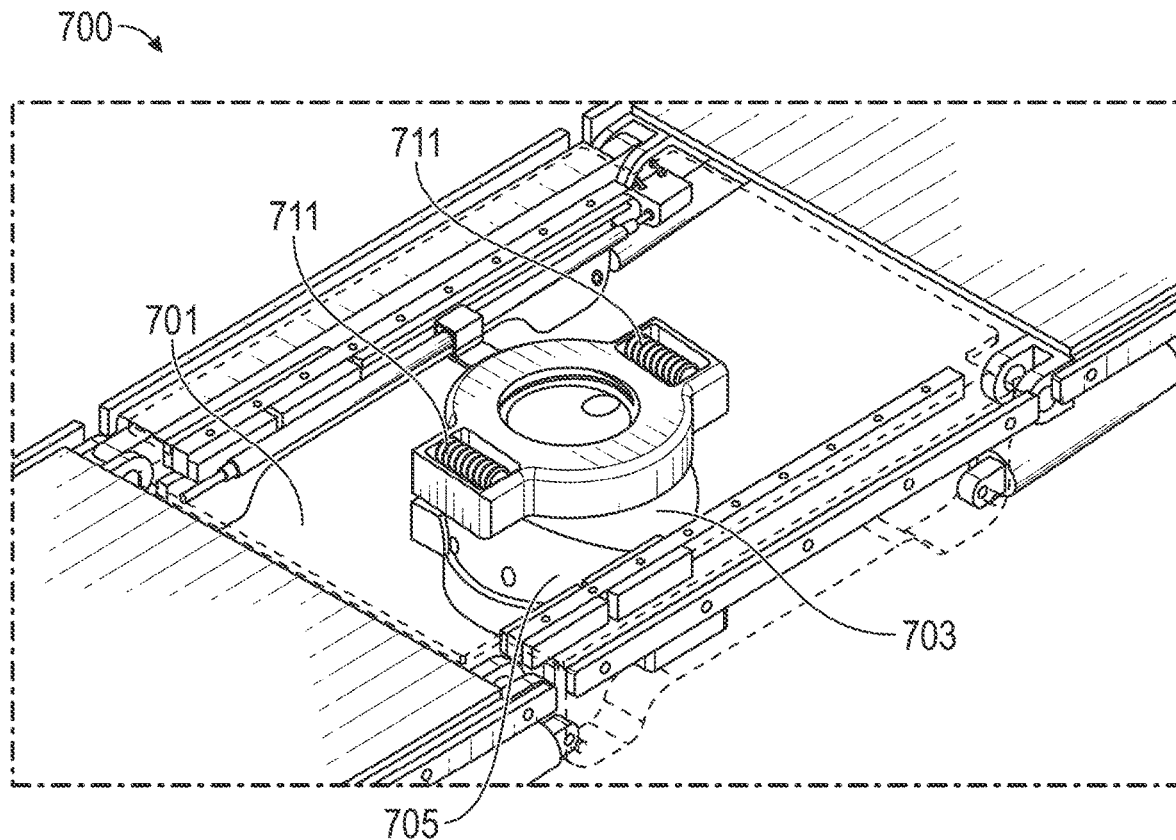
FIG. 33E is a top isometric view of the orthodrome tilt mechanism of FIG. 33A installed in a patient platform of a robotic medical system.

FIGS. 33D and 33E illustrate a top view of the tilt mechanism 700 of FIGS. 33A-33C. As illustrated, the tilt mechanism 700 can use twin worm drives 711 to actuate the top and bottom axes while the angled swivel located in the center is actuated via a harmonic drive. In some embodiments, only a single worm drive 711 is included. In some embodiments, the twin worm drives 711 can be driven by motors. Other mechanisms can also be used, such as any sort of motor and gearbox connected to the joint. Spur, planetary, cable or timing belts can all also be used as alternatives to the worm drives 711. Concerted motion of the top and bottom axes in a direction opposite to the angled axis creates an angulation at the table top. By rotating these three axes at different rates, different combinations of angles may be achieved.

One advantage of the tilt mechanism 700 is that much of the mechanism and actuation is contained within an incredibly small envelope. In many other designs, some aspect of the lateral and longitudinal tilt mechanisms normally exist in, on, or around the column, but this tilt mechanism 700 allows for all associated mechanisms and motors to be neatly packaged above the column. The tilt mechanism 700 may be an electromechanical system. Hydraulic systems can be provided in potentially smaller packages, but it can be difficult for an electromechanical system to compete with the power and size of a hydraulic system of similar size. Given the torque requirements of supporting a patient with a safety factor, the tilt mechanism 700 provides a very small and robust package.

3. Implementing Systems and Terminology.

Implementations disclosed herein provide systems, methods, and devices for robotic medical systems that include patient platforms. In particular, implementations disclosed herein provide systems, methods, and devices for lateral and/or longitudinal tilt mechanisms for patient platforms of robotic medical systems.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The phrases referencing specific computer-implemented processes and functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

The invention claimed is:

1. A tilt mechanism for a medical platform, the tilt mechanism comprising:
   a tilt plate;
   a linear actuator coupled to the tilt plate;
   a gimbal coupled to the tilt plate;
   a linear guide coupled to the gimbal and extending along a first axis;
   a motor coupled to the tilt plate and configured to drive the linear actuator; and
   a pivot housing being configured to translate along the linear guide in response to a linear force from the linear actuator, wherein translation of the pivot housing is configured to tilt the tilt plate relative to the gimbal.

2. The tilt mechanism of claim 1, wherein the pivot housing is further configured to pivot relative to the linear guide as the pivot housing translates along the linear guide.

3. The tilt mechanism of claim 1, wherein the linear actuator applies the linear force in a direction along a second axis.

4. The tilt mechanism of claim 3, wherein the first axis and the second axis are not parallel.

5. The tilt mechanism of claim 1, wherein the tilt plate is configured to pivot relative to the gimbal about a pivot axis, and the pivot axis is configured to translate relative to the gimbal along the first axis.

6. The tilt mechanism of claim 1, wherein the linear guide comprises a first set of rails, and wherein the tilt mechanism further comprises a second linear guide attached to the tilt plate and having a second set of rails.

7. The tilt mechanism of claim 6, wherein the first set of rails are positioned between the second set of rails.

8. The tilt mechanism of claim 1, wherein:
the tilt plate is attached to a patient platform; and
the gimbal is attached to a column that supports the patient platform.

9. The tilt mechanism of claim 1, wherein the gimbal is attached to the tilt plate.

10. A robotic medical system, comprising:
a patient platform configured to support a patient during a medical procedure;
a column supporting the patient platform; and
a tilt mechanism connecting the column to the patient platform, the tilt mechanism comprising:
a lateral tilt mechanism configured to pivot the patient platform about a lateral tilt axis of the patient platform, wherein the lateral tilt mechanism comprises:
a tilt plate attached to the patient platform;
a motor mounted on the tilt plate and configured to rotate a lead screw to apply a linear force to a pivot housing, wherein the pivot housing comprises a screw nut housing mounted on the lead screw and rotation of the lead screw is configured to pivot the patient platform about the lateral tilt axis of the patient platform; and
a longitudinal tilt mechanism configured to pivot the patient platform about a longitudinal tilt axis of the patient platform.

11. The system of claim 10, wherein the lateral tilt mechanism and the longitudinal tilt mechanism are configured to be operated simultaneously.

12. The system of claim 10, wherein the lateral tilt mechanism is positioned on top of the longitudinal tilt mechanism.

13. The system of claim 10, wherein the lateral tilt mechanism comprises:
a first linear guide attached to a gimbal, wherein the first linear guide extends along a first axis and the pivot housing is configured to translate along the first linear guide; and
a second linear guide attached to the tilt plate, wherein the second linear guide extends along a second axis and the pivot housing is configured to translate along the second linear guide,
wherein application of the linear force to the pivot housing tilts the tilt plate relative to the gimbal by causing the pivot housing to translate along the first linear guide and the second linear guide.

14. The system of claim 13, wherein the lead screw applies the linear force in a direction that is parallel to the second axis.

15. The system of claim 13, wherein the first axis and the second axis are not parallel.

16. The system of claim 13, wherein:
the tilt plate is configured to pivot relative to the gimbal about the lateral tilt axis, and the lateral tilt axis is configured to translate relative to the gimbal along the first axis.

17. The system of claim 13, wherein the longitudinal tilt mechanism comprises:
a longitudinal tilt linkage extending between the column and the gimbal; and
an actuator configured to actuate the longitudinal tilt linkage to pivot the gimbal relative to the column to cause the patient platform to tilt about the longitudinal tilt axis.

18. The system of claim 17, wherein the actuator comprises a longitudinal linear actuator configured to translate along an axis of the column to actuate the longitudinal tilt linkage.

19. The system of claim 13, wherein the gimbal is attached to the tilt plate.

20. The system of claim 13, wherein the gimbal is configured to allow the patient platform to pivot in a lateral direction about the lateral tilt axis and in a longitudinal direction about the longitudinal tilt axis.

* * * * *